(12) United States Patent
Soifer et al.

(10) Patent No.: US 12,245,884 B2
(45) Date of Patent: Mar. 11, 2025

(54) STETHOSCOPE DIGITAL ADAPTER CONFIGURED TO ENHANCE USABILITY OF AN ACOUSTIC STETHOSCOPE

(71) Applicant: Gregg Soifer, Dothan, AL (US)

(72) Inventors: Gregg Soifer, Dothan, AL (US); Adam Wasti, Johns Creek, GA (US)

(*) Notice: Subject to any disclaimer, the term of this patent is extended or adjusted under 35 U.S.C. 154(b) by 131 days.

(21) Appl. No.: 17/012,991

(22) Filed: Sep. 4, 2020

(65) Prior Publication Data
US 2022/0071587 A1    Mar. 10, 2022

(51) Int. Cl.
*A61B 7/04*      (2006.01)
*A61B 5/00*      (2006.01)
*H04R 1/46*      (2006.01)

(52) U.S. Cl.
CPC .............. *A61B 7/04* (2013.01); *A61B 5/6848* (2013.01); *A61B 5/6884* (2013.01); *A61B 5/742* (2013.01); *H04R 1/46* (2013.01); *A61B 2562/028* (2013.01)

(58) Field of Classification Search
CPC ....... A61B 7/04; A61B 5/6848; A61B 5/6884; A61B 5/742; A61B 2562/028; H04R 1/46
See application file for complete search history.

(56) References Cited

U.S. PATENT DOCUMENTS

| | | | |
|---|---|---|---|
| 11,234,597 B1* | 2/2022 | Farr | H04N 5/2256 |
| 2015/0190110 A1* | 7/2015 | Chong | A61B 7/003 600/528 |
| 2021/0282739 A1* | 9/2021 | Eshel | A61B 5/6803 |

FOREIGN PATENT DOCUMENTS

GB        2369434 A  *  5/2002  .............. A61B 7/02

* cited by examiner

*Primary Examiner* — Andrew Sniezek

(57) ABSTRACT

Disclosed is a stethoscope digital adapter configured to enhance usability of an acoustic stethoscope. The stethoscope digital adapter may include a body comprising an exterior shell configured to form an interior space. Further, the body may include a microphone disposed in the interior space. Further, the microphone may be configured to convert an acoustic wave into an electrical sound signal. Further, the body may include an electrical interconnect electrically coupled to the microphone. Further, the electrical interconnect may be configured to be electrically coupled with an external electronic device configured to process the electrical sound signal. Further, the body may include a conduit attached to the exterior shell. Further, the stethoscope digital adapter may include a fastener attached to the body.

21 Claims, 25 Drawing Sheets

STETHOSCOPE DIGITAL ADAPTER CONFIGURED TO ENHANCE USABILITY OF AN ACOUSTIC STETHOSCOPE

FIELD OF THE INVENTION

Generally, the present disclosure relates to the field of stethoscope. More specifically, the present disclosure relates to a stethoscope digital adapter configured to enhance usability of an acoustic stethoscope.

BACKGROUND OF THE INVENTION

There are a variety of digital stethoscopes in the market already that can store/record heart and lung sound data either in the stethoscope itself or transmitted to another device connected via Bluetooth or wire connections.

In some advanced digital stethoscopes, a software package is included that can be used to display the audio signal in the computer screen and from there have the doctors/clinicians analyze the sounds to determine the patient's health condition.

With all these advanced features available in today's digital stethoscopes, there are still some shortcomings that make it hard for patients to do self-assessment at home and to share the data recordings to his/her doctor or healthcare provider as he desired to.

Further, some conventional digital stethoscopes and accompanying software applications are technically challenging for patients and doctors as well.

Therefore, there is a need for improved stethoscope digital adapter configured to enhance usability of an acoustic stethoscope that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed is a stethoscope digital adapter configured to enhance usability of an acoustic stethoscope. The stethoscope digital adapter may include a body comprising an exterior shell configured to form an interior space. Further, the body may include a microphone disposed in the interior space. Further, the microphone may be configured to convert an acoustic wave into an electrical sound signal. Further, the body may include an electrical interconnect electrically coupled to the microphone. Further, the electrical interconnect may be configured to be electrically coupled with an external electronic device configured to process the electrical sound signal. Further, a part of the electrical interconnect may be disposed on the exterior shell. Further, the body may include a conduit attached to the exterior shell. Further, the conduit may include a first conduit opening and a second conduit opening and a conduit channel fluidly connecting the first conduit opening to the second conduit opening. Further, the first conduit opening may be acoustically coupled to the microphone. Further, the second conduit opening may be configured to be acoustically coupled to a tube of the acoustic stethoscope. Further, the stethoscope digital adapter may include a fastener attached to the body. Further, the fastener may be configured to removably fasten the body to the tube of the acoustic stethoscope.

According to some embodiments, a stethoscope head assembly is disclosed. The stethoscope head assembly may include a chest piece. Further, the chest piece may include a cylindrical body comprising an inner space. Further, the chest piece may include a diaphragm disposed on a first side of the cylindrical body. Further, the diaphragm may be configured to receive a first acoustic wave characterized by a first frequency. Further, the chest piece may include a bell disposed on a second side of the cylindrical body. Further, the second side is opposing the first side. Further, the bell may be configured to receive a second acoustic wave characterized by a second frequency. Further, the second frequency may be lower than the first frequency. Further, the chest piece may include a stem connected to the cylindrical body. Further, the stem may include a stem opening and a stem channel fluidly connecting the stem opening to the inner space. The stethoscope head assembly may include a body. Further, the body may include an exterior shell configured to form an interior space. Further, the body may include a microphone disposed in the interior space. Further, the microphone may be configured to convert an acoustic wave into an electrical sound signal. Further, the body may include an electrical interconnect electrically coupled to the microphone. Further, the electrical interconnect may be configured to be electrically coupled with an external electronic device configured to process the electrical sound signal. Further, a part of the electrical interconnect may be disposed on the exterior shell. Further, the body may include a conduit attached to the exterior shell. Further, the conduit may include a first conduit opening and a second conduit opening and a conduit channel fluidly connecting the first conduit opening to the second conduit opening. Further, the first conduit opening may be acoustically coupled to the microphone. Further, the second conduit opening may be configured to be acoustically coupled to the stem opening.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION OF THE INVENTION

Figure 1:
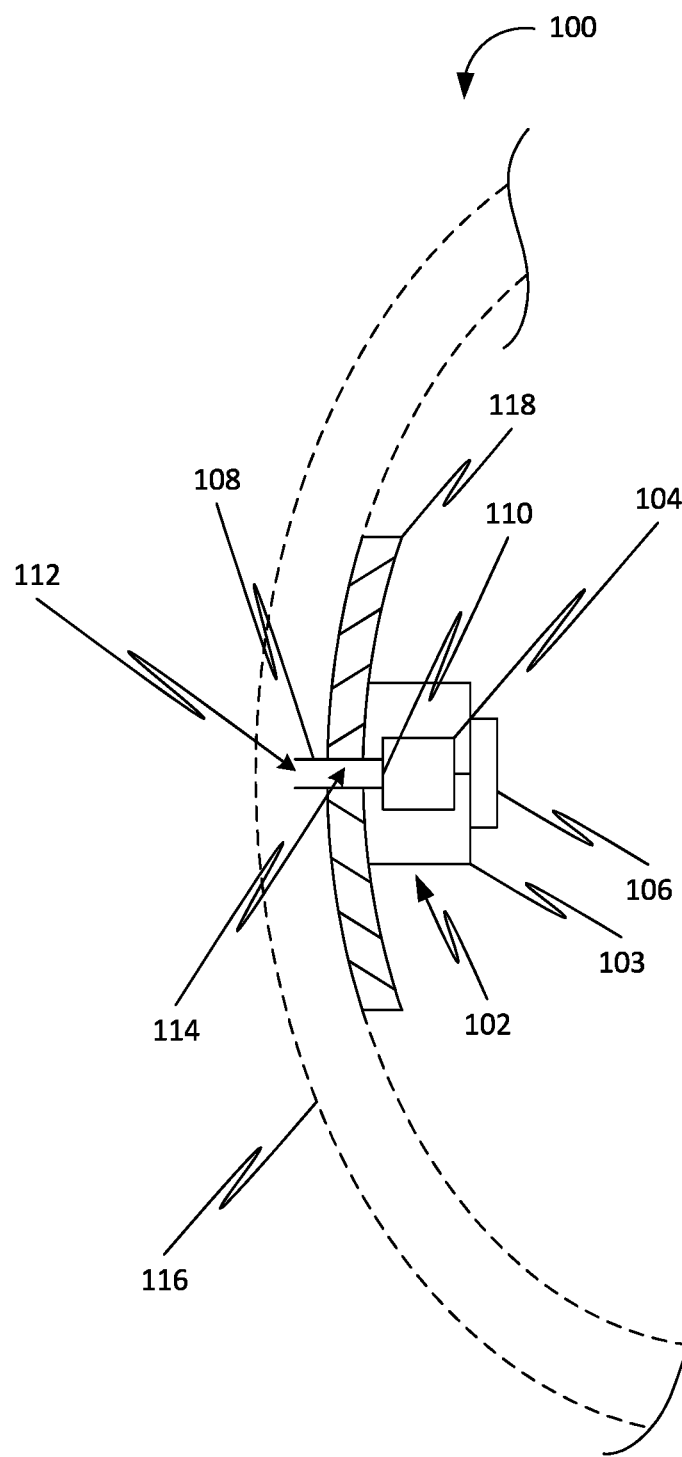
FIG. 1 is a side cross-section view of a stethoscope digital adapter configured to enhance usability of an acoustic stethoscope, in accordance with some embodiments.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of stethoscope digital adapter configured to enhance usability of an acoustic stethoscope, embodiments of the present disclosure are not limited to use only in this context.

Overview:

Further, the present disclosure describes a smart stethoscope for remote patient management. The disclosed smart stethoscope is patient-friendly starting from data gathering of heart/lung/stomach sounds, saving the data, and then sharing the files to remote devices. Further, the ease-of-use of the disclosed smart stethoscope eliminates the need for patient to seek help/assistance and give independence as much as possible.

Further, the disclosed smart stethoscope covers shortcomings of conventional digital stethoscopes. Further, the disclosed smart stethoscope includes features such as data sharing controlled by the user (patient/doctor), software-assisted classification of the sound, auto start/stop of recording sound data, smart tagging of sound data in reference to the patient's health condition and manual tagging/commenting of patient's current condition/feeling as part of the logs.

Further, the disclosed smart stethoscope assists patients with pre-existing health conditions, patients with limited resources and patients with limited resources. The patients with existing health problems need special assistance to determine if they are "unhealthy but normal" heart/lung readings are getting abnormal/worse than before. The doctors have to refer to previous readings to determine that. The disclosed smart stethoscope will automate that process so that patients with pre-existing problems can also use the disclosed smart stethoscope.

Further, the humanitarian objective of the disclosed smart stethoscope is to cut the cost of digitizing the human sound to make it viable for the less fortunate. The disclosed smart stethoscope will enhance the capability for remote/tele-healthcare services and will lessen the instances of global uneducated self-diagnose at the same time.

Further, the simplicity of using the disclosed smart stethoscope is as easy as connecting a stethoscope earpiece to a mobile phone. This form-factor of a digital stethoscope is not overwhelming and engage patients to use it more than rejecting.

Further, the disclosed digital stethoscope is a dual head stethoscope with a MEMS microphone digital adapter that connects to the mobile phone via headset port. In an extended version, the MEMS microphone digital adapter can be connected to an existing analog stethoscope. Further, the integration to the stethoscope tube requires minimal effort and intervention. There is no need to cut the tube for the adapter to be inserted in (or bridged in).

Further, a mobile application with a minimalistic user interface that requires only point/touch and click for navigation and operations (reading, saving, tagging and sharing data) is disclosed. In an extended version, the mobile application can be upgraded to the smart version that uses Artificial Intelligence (AI) and Spectrogram Analysis of audio waves. This smart version can auto compare current readings from patient's previous files as well as from reference data that comes with the AI. The AI and Spectrogram combination drives the intelligence of the Remote Patient Management System.

Further, the disclosed Smart Digital Stethoscope can inter-operate with existing analog stethoscopes that doctors are accustomed with. The software application is created for the two major mobile platforms (Android and IoS) to cover majority mobile users globally.

Further, the disclosed digital stethoscope helps increasing data visibility of the data collected by the stethoscope. Further, the data can be traced all throughout its lifespan, from the creation down to distribution and archiving/delete. Since a clear method/process of managing data is provided, the user can execute the same process over and over again without violating (or misdoing) data privacy rules and regulations. Since traceability and repeatability is in place, the disclosed digital stethoscope promotes data accountability. The user has the first right of ownership and has the regulatory power for data sharing based on the HIPAA and other Privacy rules set in the SMART Patient Management software.

Further, with all the automated features linked to the data management and security, plus the extensible hardware capacity of mobile devices, the sustainability of maintaining the integrity and viability of patient data are achievable. Conventional stand-alone digital stethoscope is limited by the internal hardware components which are (mostly) not upgradeable and has no room for extensions.

Further, the Stethoscope for Remote Patient Management (SMART) is designed with a holistic approach. This disclosure considers users, process and the hardware components as one unit to achieve inclusivity, ease of use, sustainability and maintainability.

According to some embodiments, the digital stethoscope requires no power. Further, the battery is not required for the digital stethoscope head (even in the extended version—digital stethoscope adapter). Further, the MEMS microphone module derives its power from the mobile phone/device via earphone port.

According to some embodiments, the digital stethoscope uses a special wide-range MEMS microphone. Further, the MEMS microphone used in this disclosure has a range of 10 Hz to 10 kHz. This is not the usual frequency range found in everyday devices with the range of 20 Hz to 20 kHz. Further, this MEMS microphone can capture very well the low frequency range of heart that ranges from 20 Hz to 150/500 Hz as well as the lung's low/mid/high frequency bands than ranges from 100 Hz to 1.2 kHz.

According to some embodiments, the mobile application can shift the frequency range of raw data. Further, the mobile application can shift the raw data from 10-500 Hz to 20-600

Hz. Further, shifting the raw data by 10 Hz will allow users to hear more clearly the heartbeat since human's ear can only hear infrasound starting at 20 Hz.

According to some embodiments, the mobile application can enhance heart and lung sounds via white noise cancellation. Further, raw data coming from MEMS microphone are barely white noise when unfiltered. Further, the mobile application will automatically enhance the raw data by increasing the gains from 10 Hz to 500 Hz, then doing the reverse for 700 Hz and above.

According to some embodiments, the mobile application can save the enhanced sound with specific tags. Further, the mobile app will save the sound data to a filename having the current date/time of the device and the sound classification (heart, lung, or stomach). Further, the "current condition" tag and other customized tags will be added to the filename. This will make data/file management more intuitive and will not require reference data tables as well. (The "current condition" is selected by the patient from the options listed during the save function.)

According to some embodiments, the mobile application guides the user on the proper way of using the stethoscope. Further, audio/visual instructions will present the steps that users can follow to properly use the stethoscope. Further, there are audio/visual feedback mechanism that indicates success/failure in processing sound data. Further, timer is started/stopped automatically or manually based on user preference.

According to some embodiments, the disclosed SMART system can auto-detect the quality of sound recording. Further, user will be prompted by the system to indicate if the recorded sound is of good quality or not. Further, user will be prompted by the system if the length of the sound recording is not significant enough for health diagnosis.

According to some embodiments, the disclosed SMART system can auto-detect the type of sound recording. Further, user will be assisted and/or corrected if the recorded data is for heart, lung or stomach.

According to some embodiments, the disclosed SMART system can learn the user's normal sound readings. Further, patient with pre-existing health conditions have a heart/lung/stomach sound data that differs from the average normal healthy sound. Further, the SMART system uses AI to automatically learn what is "normal" and "abnormal" readings for patient with pre-existing health conditions.

According to some embodiments, the disclosed SMART system can determine health problem based on the sound readings. Further, SMART system uses AI to compare the user's sound data against known health conditions. Further, SMART system auto-tag the sound recording with the AI prediction so doctors can have a second look at it and finalized diagnosis.

According to some embodiments, the disclosed SMART system can determine if the abnormal reading is critical. Further, SMART system can automatically send alert messages to the user and to selected remote destinations as authorized by the user.

According to some embodiments, the disclosed SMART system can determine if monitoring program is being followed or not. Further, SMART system can store monitoring program that is assigned by doctor to patient. Further, Alert and notification messages will prompt the user for compliance.

According to some embodiments, the disclosed SMART system can determine if the abnormal reading is critical. Further, SMART system can automatically determine critical sound readings and send alert messages to the user and to selected remote destinations as authorized by the user.

According to some embodiments, the disclosed SMART system can log all data handling for HIPAA compliance. Further, SMART system automatically keep track of data processing to comply with HIPAA requirements.

According to some embodiments, the disclosed SMART system can do analytics of all sound data. Further, SMART system can show the historical data in a graph format for user to understand his health conditions visually.

According to some embodiments, a Stethoscope Head Assembly is disclosed. The Stethoscope Head Assembly may include a MEMS microphone that doesn't need battery as it derives power from a cellphone. Further, the Stethoscope Head Assembly may connect to mobile phone via earphone jack. Further, the MEMS microphone may operate in the frequency range: 10 Hz to 10 kHz. Further, the Stethoscope head may be interchangeable for different purposes: neonatal, infant, pediatric, cardiology, veterinary, etc.

According to some embodiments, a Stethoscope Digital Adapter Assembly is disclosed. A non-intrusive connection of stethoscope digital adapter to the main stethoscope tube eliminates cutting of the tube. Further, the MEMS microphone only needs at least 1 mm hole in the tube to sample audio sound passing through the tube from stethoscope head to the earpiece. Further, if decided to remove the digital adapter, the hole may or may not heal itself depending on the quality of the tube. Nevertheless, an emblem (a sealing) is provided to patch the hole permanently.

FIG. 1 is a side cross-section view of a stethoscope digital adapter 100 configured to enhance usability of an acoustic stethoscope, in accordance with some embodiments. The stethoscope digital adapter 100 may include a body 102 comprising an exterior shell 103 configured to form an interior space.

Further, the body 102 may include a microphone 104 disposed in the interior space. Further, the microphone 104 may be configured to convert an acoustic wave into an electrical sound signal. Accordance with some embodiments, the microphone 104 may include a MEMS microphone. Accordance with some embodiments, the microphone 104 may be characterized by a bandwidth ranging from 10 Hz to 10 kHz.

Further, the body 102 may include an electrical interconnect 106 electrically coupled to the microphone 104. Further, the electrical interconnect 106 may be configured to be electrically coupled with an external electronic device (not shown) configured to process the electrical sound signal. For example, the external electronic device may be at least one of a mobile device and a patient monitoring device. Further, a part of the electrical interconnect 106 may be disposed on the exterior shell 103.

Accordance with some embodiments, the electrical interconnect 106 may be configured to receive electrical power from the external electronic device. Further, the microphone 104 may be configured to use the electrical power to convert the acoustic wave into the electrical sound signal.

Further, the body 102 may include a conduit 108 attached to the exterior shell 103. Further, the conduit 108 may include a first conduit opening 110 and a second conduit opening 112 and a conduit channel 114 fluidly connecting the first conduit opening 110 to the second conduit opening 112. Further, the first conduit opening 110 may be acoustically coupled to the microphone 104. Further, the second conduit opening 112 may be configured to be acoustically coupled to a tube 116 of the acoustic stethoscope.

Further, the stethoscope digital adapter 100 may include a fastener 118 attached to the body 102. Further, the fastener 118 may be configured to removably fasten the body 102 to the tube 116 of the acoustic stethoscope.

Figure 2:
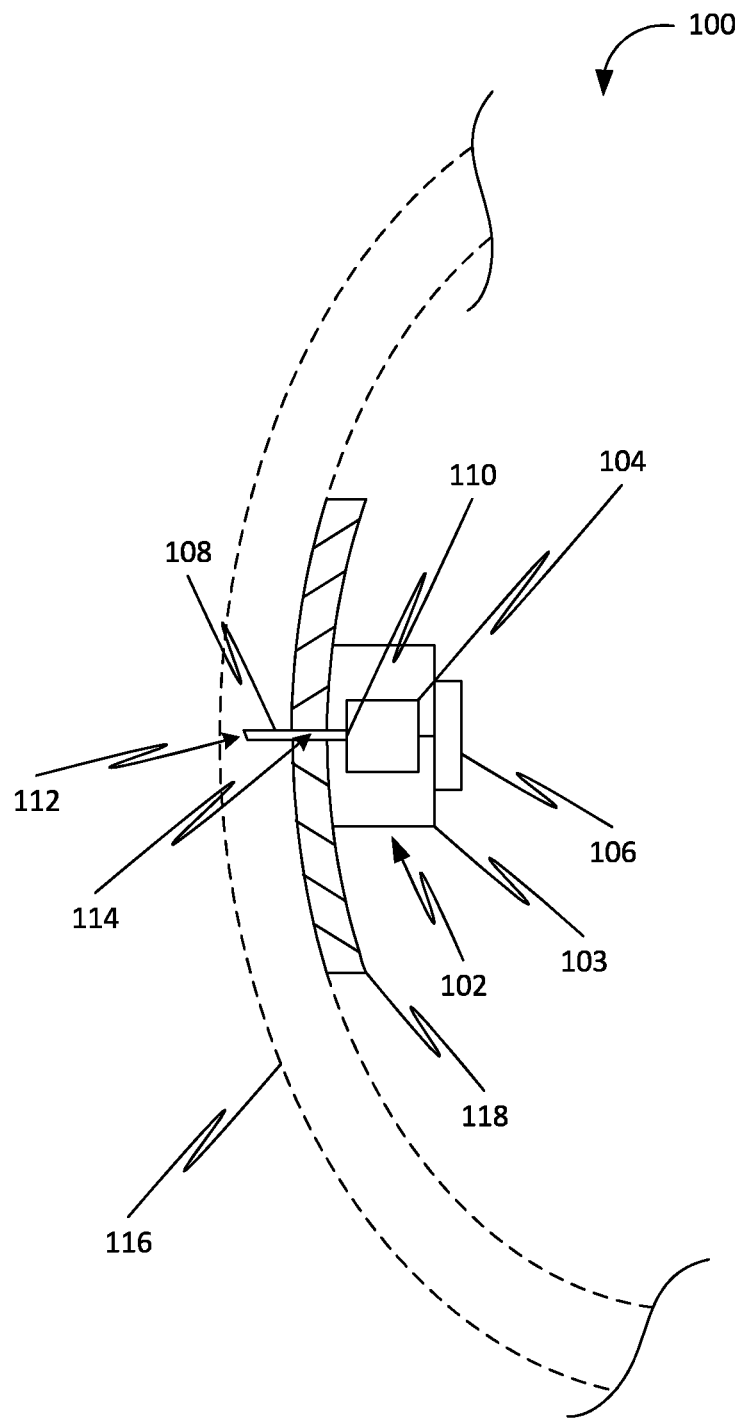
FIG. 2 is a side cross-section view of the stethoscope digital adapter configured to enhance usability of the acoustic stethoscope, in accordance with further embodiments.

In further embodiments, the conduit 108 may include a needle (as shown in FIG. 2). Accordingly, the second conduit opening 112 may be configured to pierce through the tube 116 of acoustic stethoscope creating an opening in the tube 116. In some embodiments, the opening may be at most 1 mm in diameter.

Figure 3:
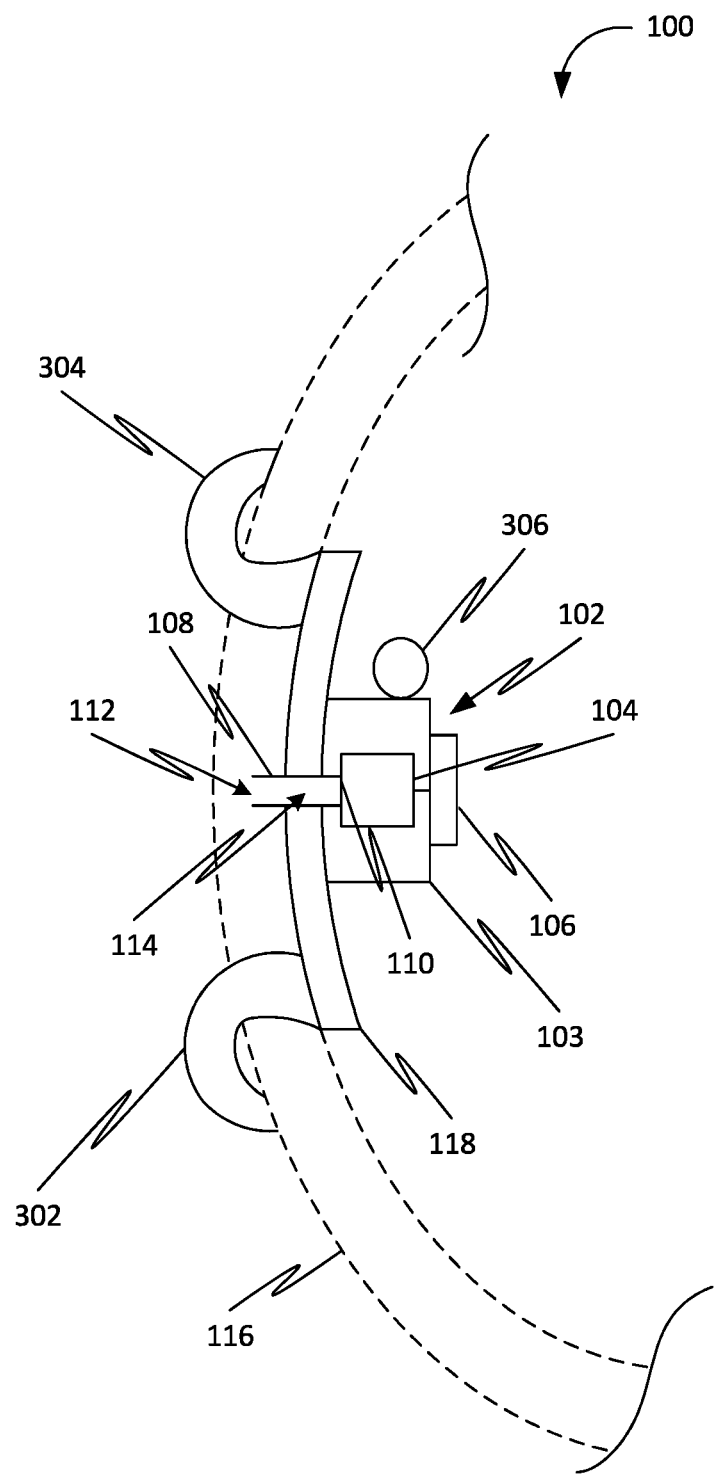
FIG. 3 is a side cross-section view of the stethoscope digital adapter configured to enhance usability of the acoustic stethoscope, in accordance with further embodiments.

In some embodiments, the fastener may include a pair of clamps 302-304 (as shown in FIG. 3. Further, a first clamp 302 of the pair of clamps 302-304 may be disposed on a left side of the body 102. Further, a second clamp 304 of the pair of clamps 302-304 may be disposed on a right side of the body 102. Further, each clamp of the pair of clamps 302-304 may be configured to receive and secure a corresponding portion of the tube 116.

Further, a sealing device 306 may be removably fastened to the body 102. Further, the sealing device 306 may be configured to seal the opening created in the tube 116 by the needle.

Figure 4:
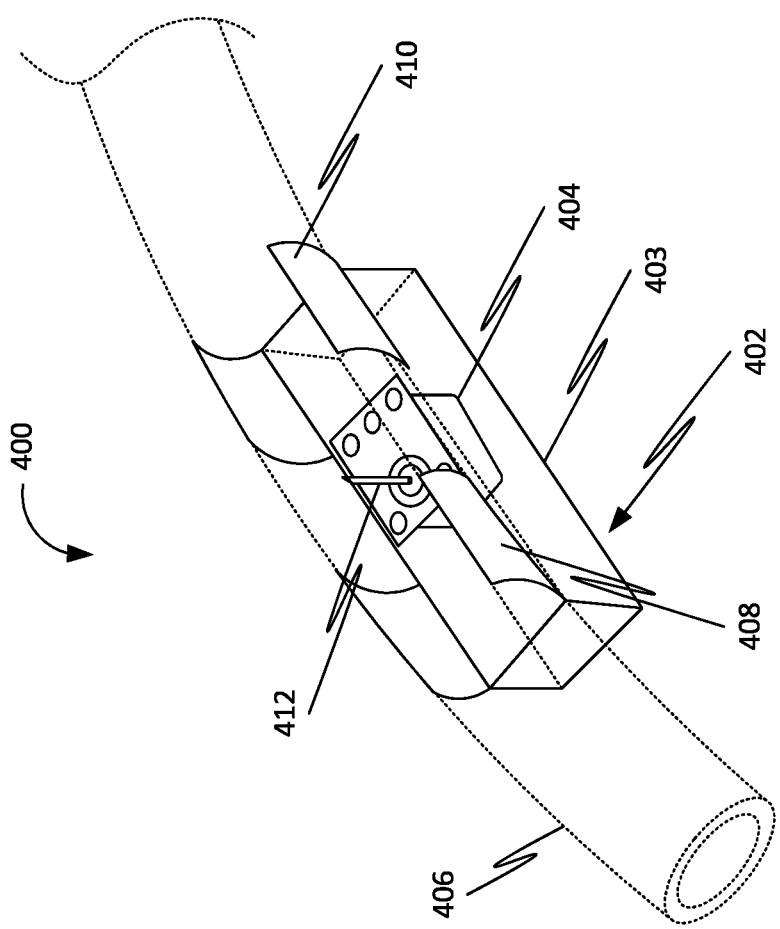
FIG. 4 is a top front perspective view of a stethoscope digital adapter configured to enhance usability of an acoustic stethoscope, in accordance with some embodiments.

FIG. 4 is a top front perspective view of a stethoscope digital adapter 400 configured to enhance usability of an acoustic stethoscope, in accordance with some embodiments. The stethoscope digital adapter 400 may include a body 402 comprising an exterior shell 403 configured to form an interior space. Further, the body 402 may include a microphone 404 disposed in the interior space. Further, the body 402 may include an electrical interconnect (not shown) electrically coupled to the microphone 404. Further, the electrical interconnect may be configured to be electrically coupled with an external electronic device (not shown) configured to process the electrical sound signal.

Further, the stethoscope digital adapter 400 may include a fastener attached to the body 402. Further, the fastener may be configured to removably fasten the body 402 to the tube 406 of the acoustic stethoscope. In some embodiments, the fastener may include a pair of clamps 408-410. Further, a first clamp 408 of the pair of clamps 408-410 may be disposed on a left side of the body 402. Further, a second clamp 410 of the pair of clamps 408-410 may be disposed on a right side of the body 402. Further, each clamp of the pair of clamps 408-410 may be configured to receive and secure a corresponding portion of the tube 406.

Further, the stethoscope digital adapter 400 may include a needle 412. Accordingly, the needle 412 may pierce through the tube 406 of the acoustic stethoscope creating an opening in the tube 406.

Figure 5:
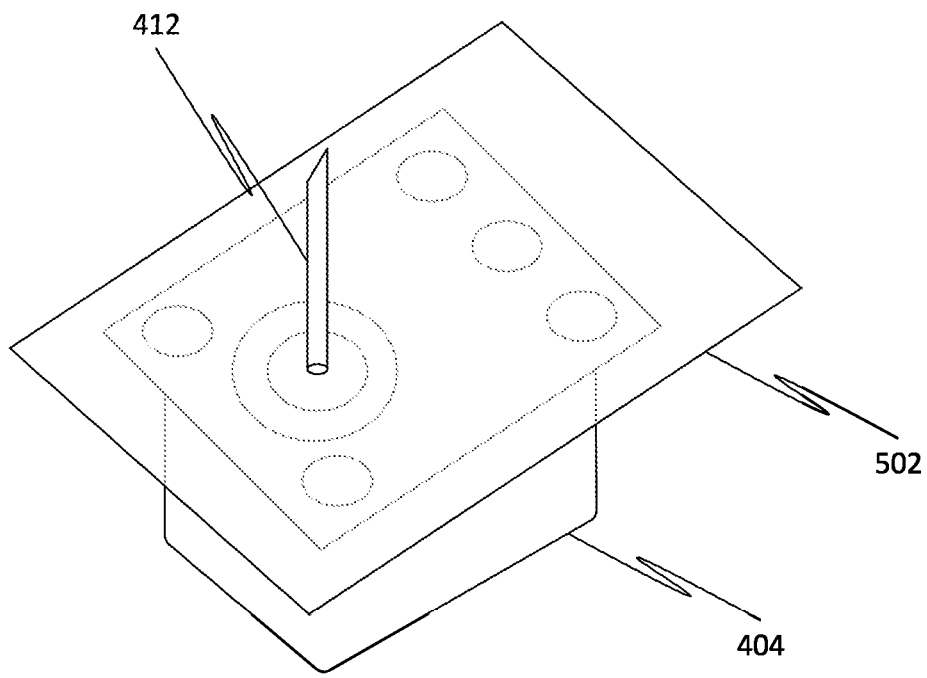
FIG. 5 is a top front perspective view of the microphone, in accordance with some embodiments.

FIG. 5 is a top front perspective view of the microphone 404, in accordance with some embodiments. Further, the microphone 404 may include an enclosure 502.

Figure 6:
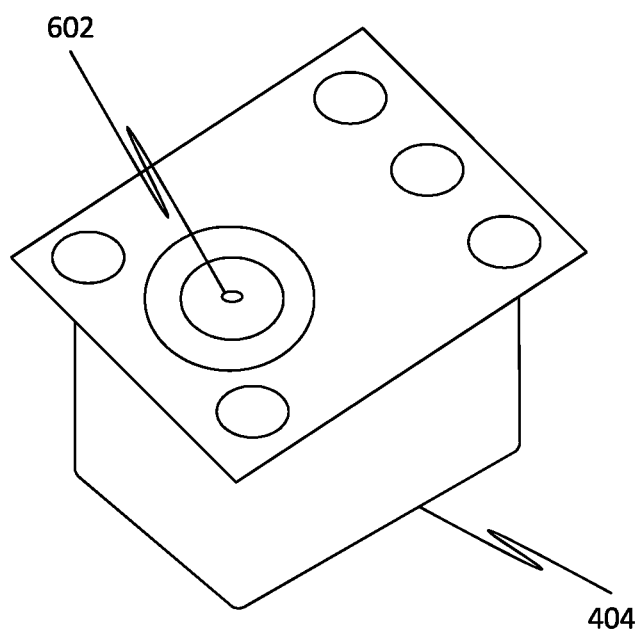
FIG. 6 is a top front perspective view of the microphone without needle and enclosure, in accordance with some embodiments.

FIG. 6 is a top front perspective view of the microphone 404 without needle and enclosure, in accordance with some embodiments. The microphone 404 includes a microphone hole 602.

Figure 7:
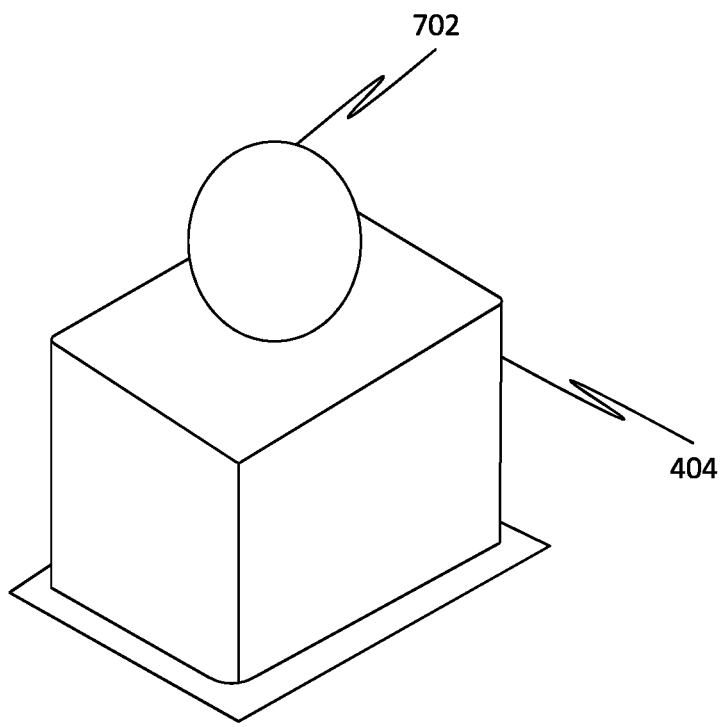
FIG. 7 is a bottom front perspective view of the microphone, in accordance with some embodiments.

FIG. 7 is a bottom front perspective view of the microphone 404, in accordance with some embodiments. Further, the microphone 404 may include a sealing device 702.

Figure 8:
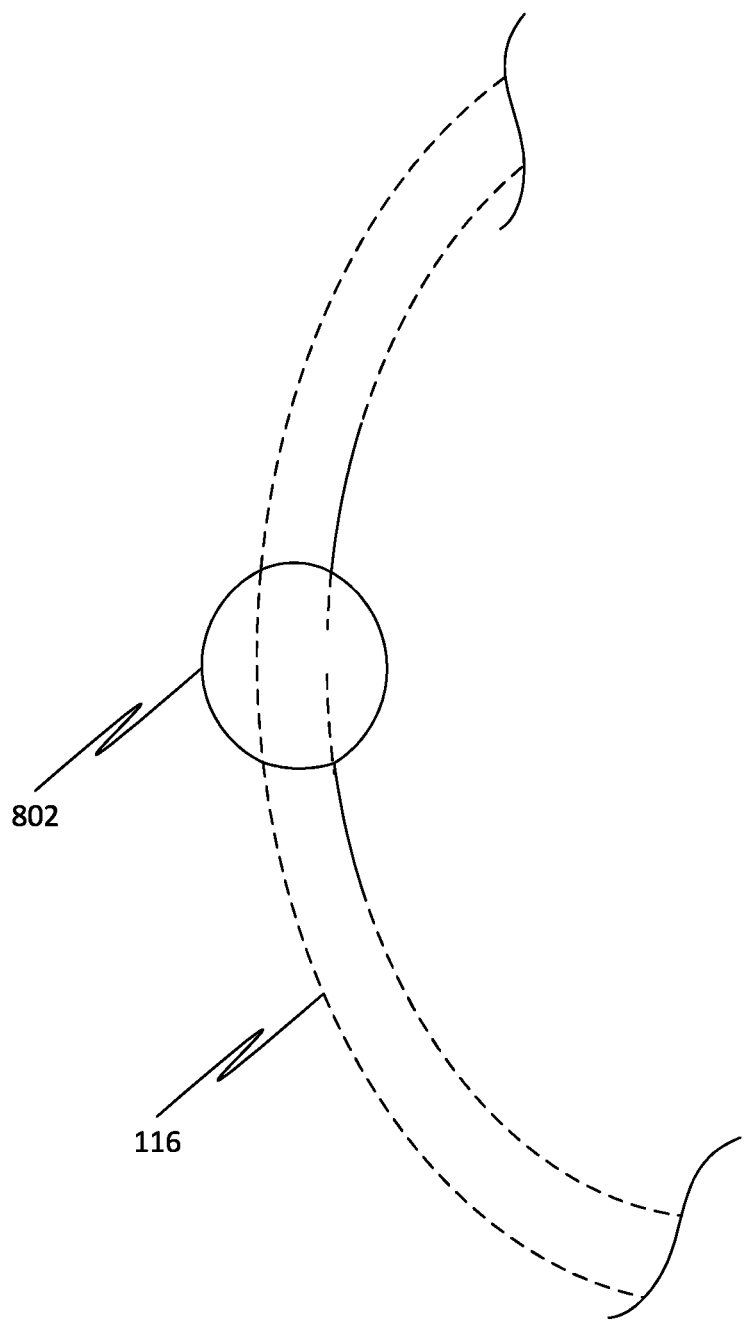
FIG. 8 is a side view of the tube with the stethoscope digital adapter removed, in accordance with further embodiments.

FIG. 8 is a side view of the tube 116 with the stethoscope digital adapter 100 removed, in accordance with further embodiments. Further, a sealing device 802 (similar to the sealing devices 306 and 702) may be removably fastened to the body 102. Further, the sealing device 802 may be configured to seal the opening created in the tube 116 by the needle (as shown in FIG. 2). Further, the sealing device 802 may be further configured to removably fasten to the tube 116 of the acoustic stethoscope.

Figure 9:
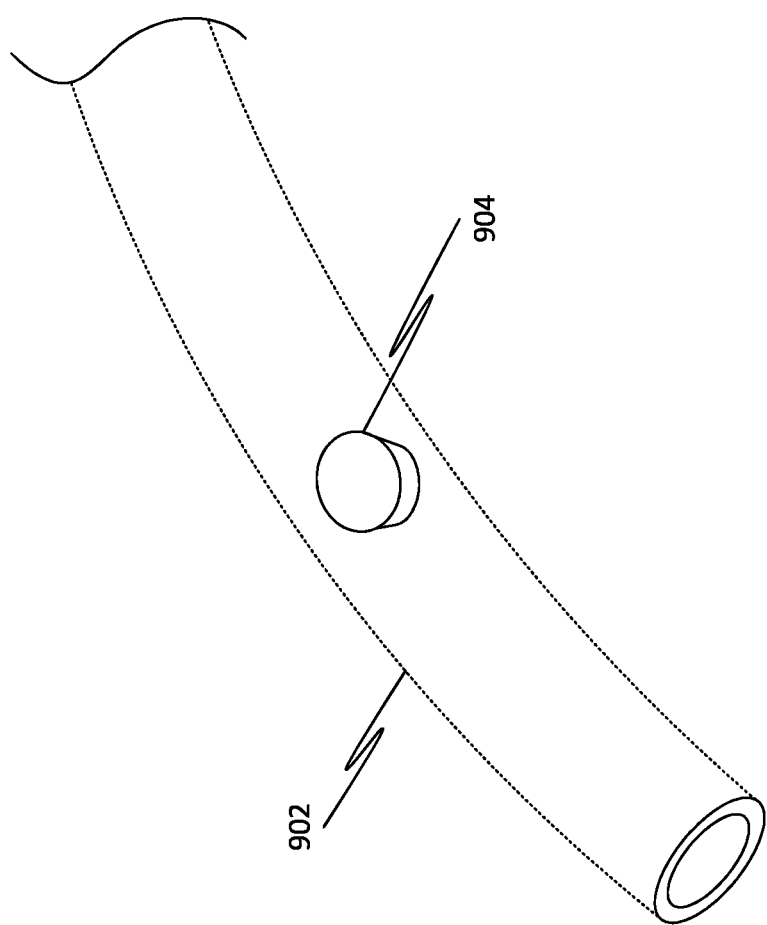
FIG. 9 is a top front perspective view of a tube of an acoustic stethoscope with a stethoscope digital adapter removed, in accordance with some embodiments.

FIG. 9 is a top front perspective view of a tube 902 of an acoustic stethoscope with a stethoscope digital adapter removed, in accordance with some embodiments. Further, a sealing device 904 (similar to the sealing devices 306 and 702) may be removably fastened to a body of the stethoscope digital adapter. Further, the sealing device 904 may be configured to seal an opening created in the tube 902 by a needle of the stethoscope digital adapter. Further, the sealing device 904 may be further configured to removably fasten to the tube 902 of the acoustic stethoscope.

Figure 10:
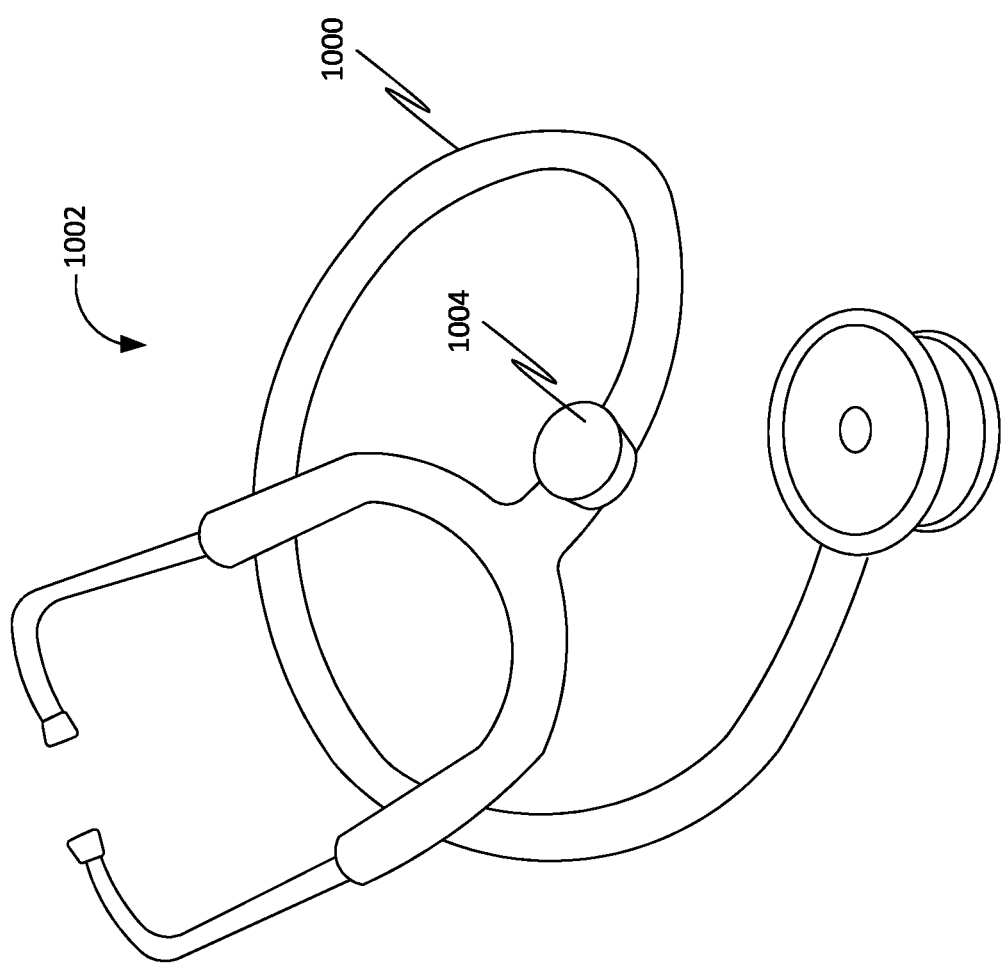
FIG. 10 is a top front perspective view of a tube of an acoustic stethoscope with a stethoscope digital adapter removed, in accordance with some embodiments.

FIG. 10 is a top front perspective view of a tube 1000 of an acoustic stethoscope 1002 with a stethoscope digital adapter removed, in accordance with some embodiments. Further, a sealing device 1004 (similar to the sealing devices 306 and 702) may be removably fastened to a body of the stethoscope digital adapter. Further, the sealing device 1004 may be configured to seal an opening created in the tube 1000 by a needle of the stethoscope digital adapter. Further, the sealing device 1004 may be further configured to removably fasten to the tube 1000 of the acoustic stethoscope 1002.

Figure 11:
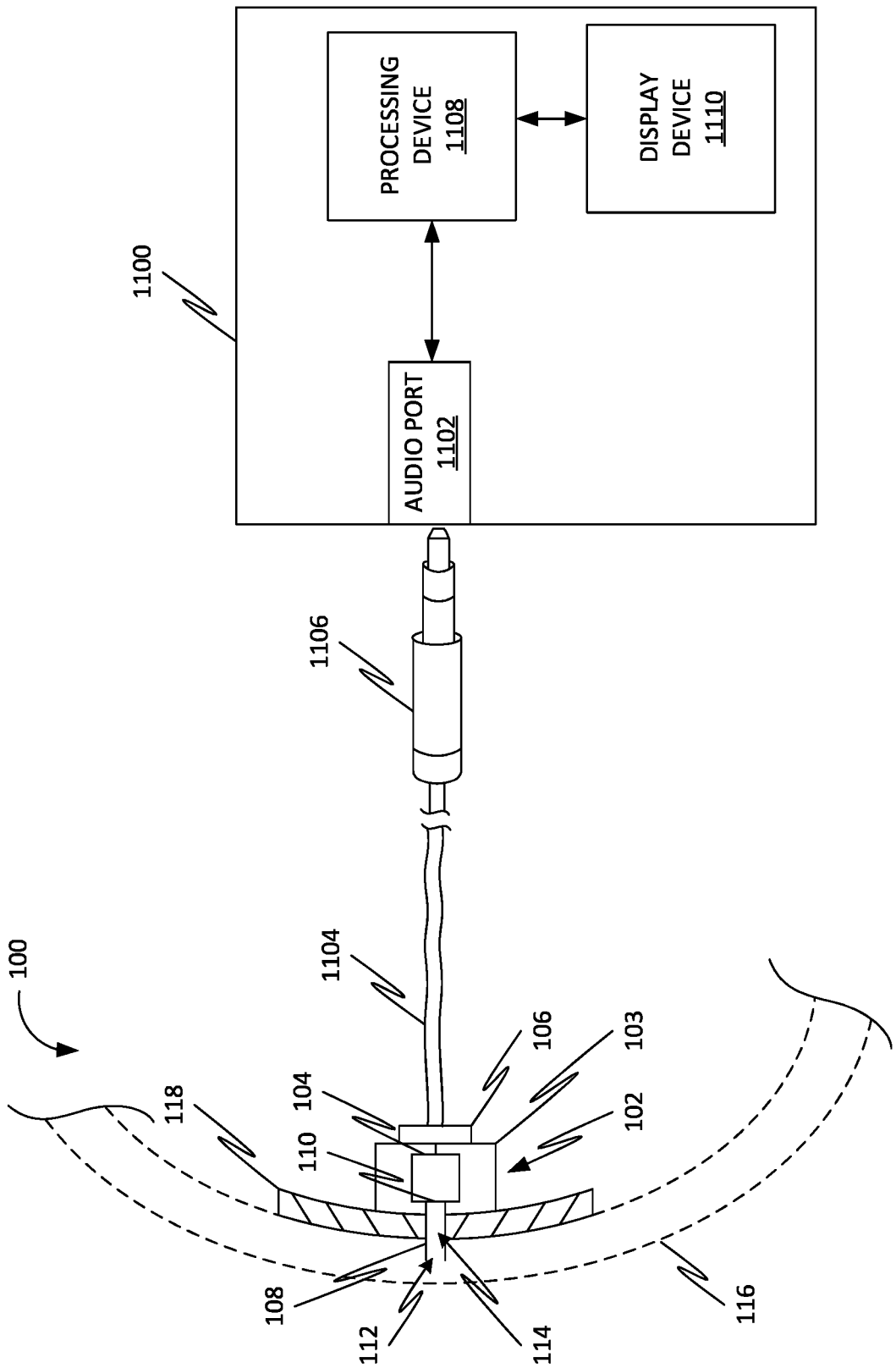
FIG. 11 is a side cross-section view of the stethoscope digital adapter with an external device, in accordance with further embodiments.

As shown in FIG. 11, the stethoscope digital adapter 100 may further include the external electronic device 1100. Further, the external electronic device 1100 may include an audio port 1102 configured to interconnect with the electrical interconnect 106. Further, the electrical interconnect 106 may include an electrical cable 1104 and an audio jack 1106 electrically connected to a distal end of the electrical cable 1104. Further, the audio jack 1106 may be configured to removably interconnect with the audio port 1102.

Further, the external electronic device 1100 may include a processing device 1108 electrically coupled to the audio port 1102. Further, the processing device 1108 may be configured to generate digital sound data based on the electrical sound signal, analyze the digital sound data and identify at least one characteristic associated with the electrical sound signal based on the analyzing.

In some embodiments, the processing device 1108 may be further configured to filter the digital sound data to cancel white noise present in the electrical sound signal.

Further, the external electronic device 1100 may include a display device 1110 communicatively coupled to the processing device 1108. Further, the display device 1110 may be configured to display the at least one characteristic.

In further embodiments, the processing device 1108 may be configured to detect a quality of the electrical sound signal based on the analyzing and generate a notification based on the quality being below a predetermined quality threshold. Further, the display device 1110 may be configured for displaying the notification. Further, the predetermined quality threshold may include a predetermined duration corresponding to the electrical sound signal.

Figure 12:
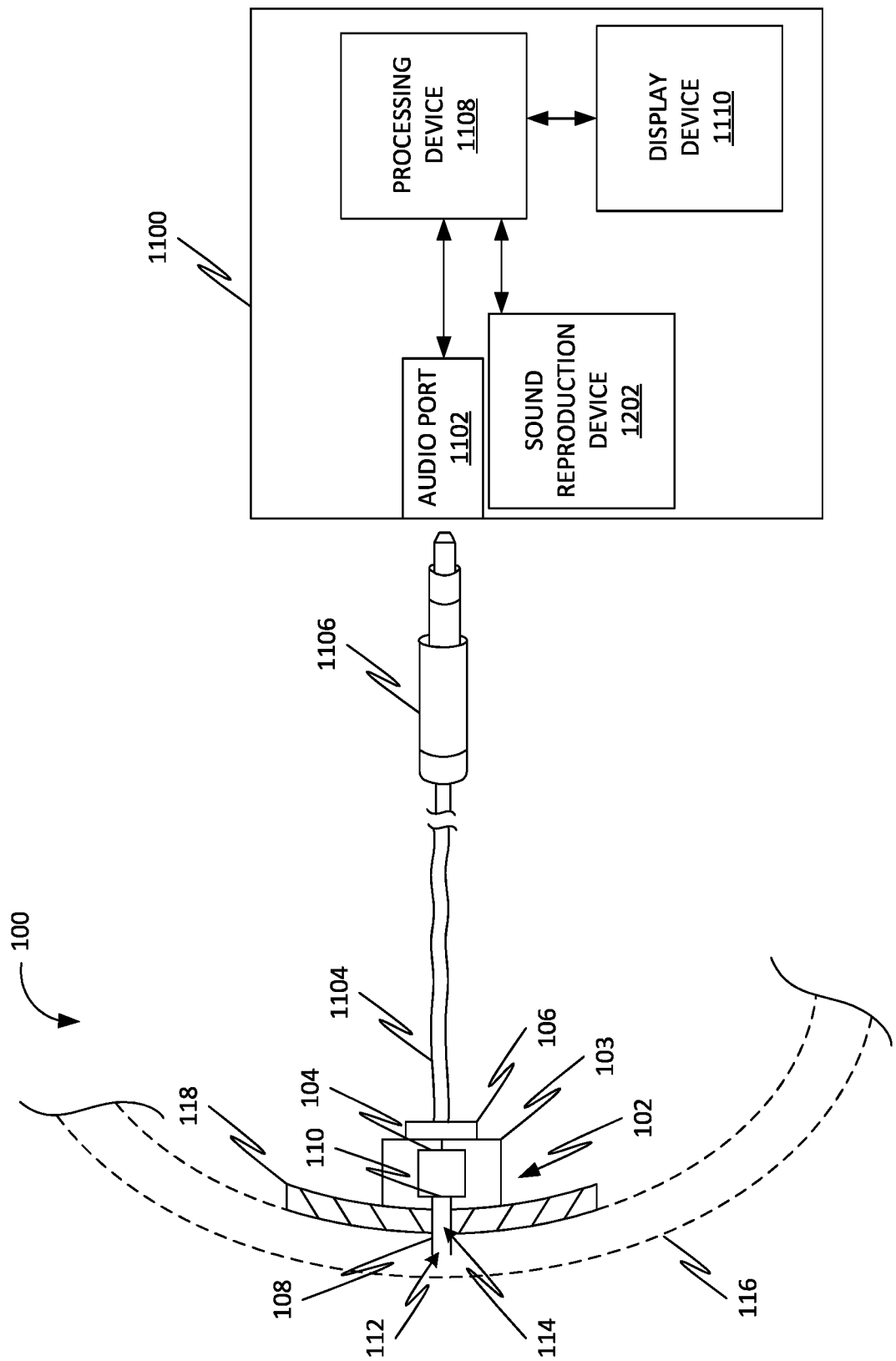
FIG. 12 is a side cross-section view of the stethoscope digital adapter with the external device, in accordance with further embodiments.

As shown in FIG. 12, the external electronic device 1100 may further include a sound reproduction device 1202 communicatively coupled to the processing device 1108. Further, the sound reproduction device 1202 may be configured to generate amplified acoustic waves based on the digital sound data. In further embodiments, the processing device 1108 may be configured to shift at least one frequency of the digital sound data from an original value to a preferred value. In further embodiments, the at least one frequency may include a band of frequencies from 10 Hz to 500 Hz, wherein the preferred value may include 20 Hz to 600 Hz.

Figure 13:
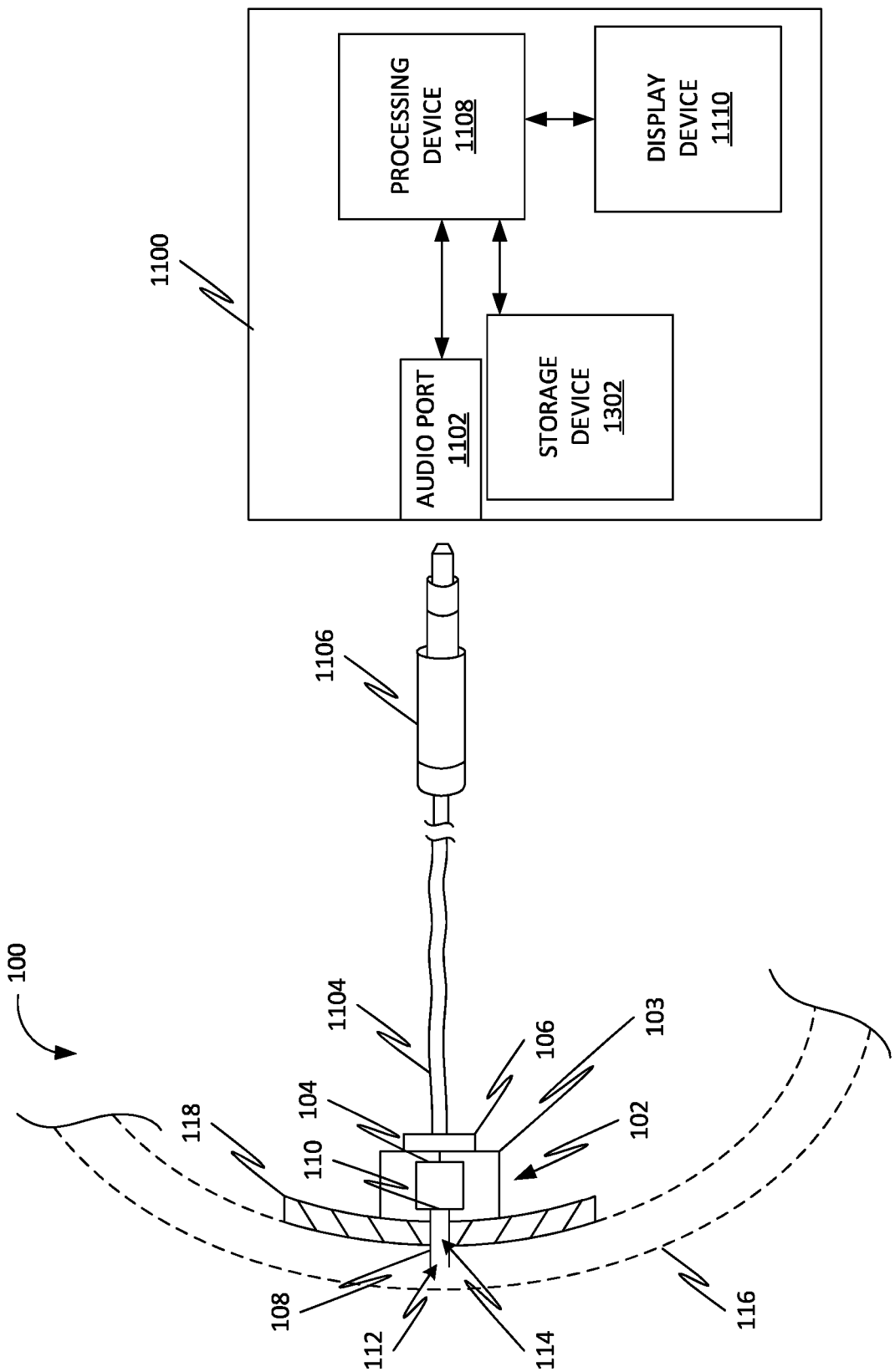
FIG. 13 is a side cross-section view of the stethoscope digital adapter with the external device, in accordance with further embodiments.

As shown in FIG. 13, the external electronic device 1100 may further include a storage device 1302 configured to save the digital sound data, the at least one characteristic and a time-stamp corresponding to the generation of the digital sound data in a data file. Further, the processing device 1108 may be further configured to generate the time-stamp based on a real-time clock.

Figure 14:
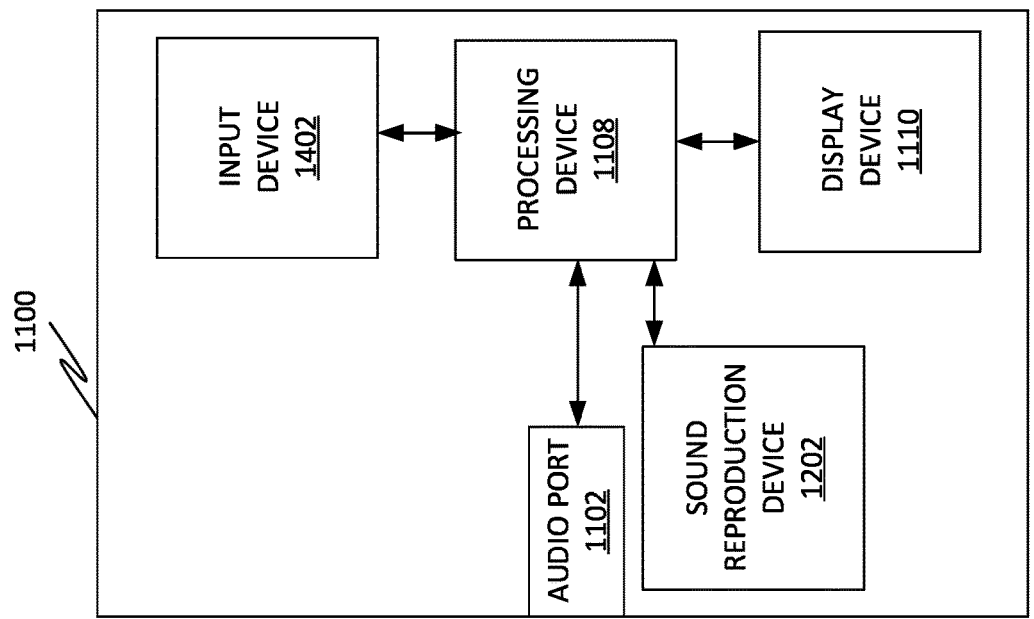
FIG. 14 is a side cross-section view of the stethoscope digital adapter with the external device, in accordance with further embodiments.
Figure 14:
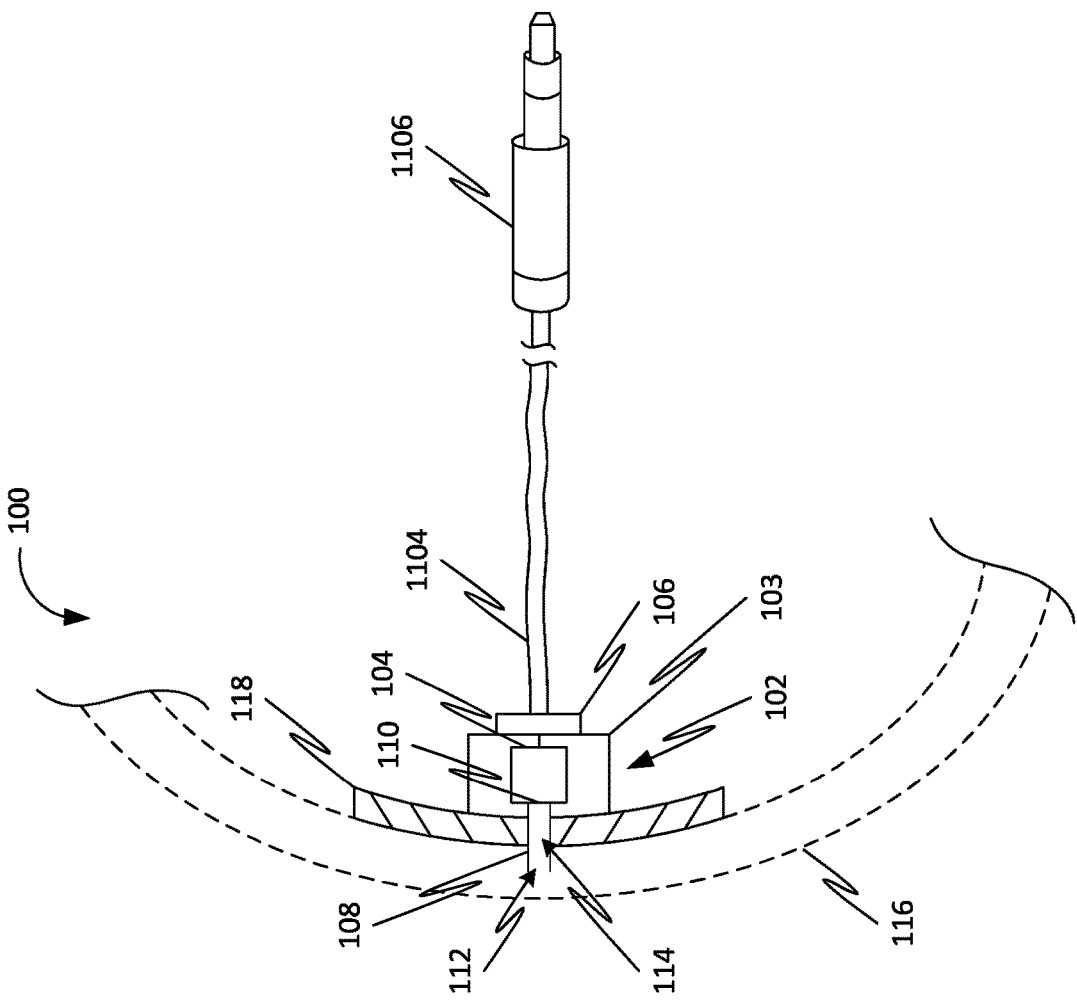

In further embodiments, the at least one characteristic may include an organ indicator associated with an organ originating the acoustic wave. Further, the processing device 1108 may be configured for generating a file name associated with the data file based on each of the time-stamp, the organ indicator and a current condition tag. Further, the external electronic device 1100 may include an input device 1402 (shown in FIG. 14) communicatively coupled to the processing device 1108. Further, the input device 1402 may be configured to receive the current condition tag. Further, the current condition tag may be indicative of a medical condition of the user. Further, the processing device 1108 may be configured for generating the at least one characteristic based further on the current condition tag. Further, the at least one characteristic may include one of a normal sound indication and an abnormal sound indication.

Figure 15:
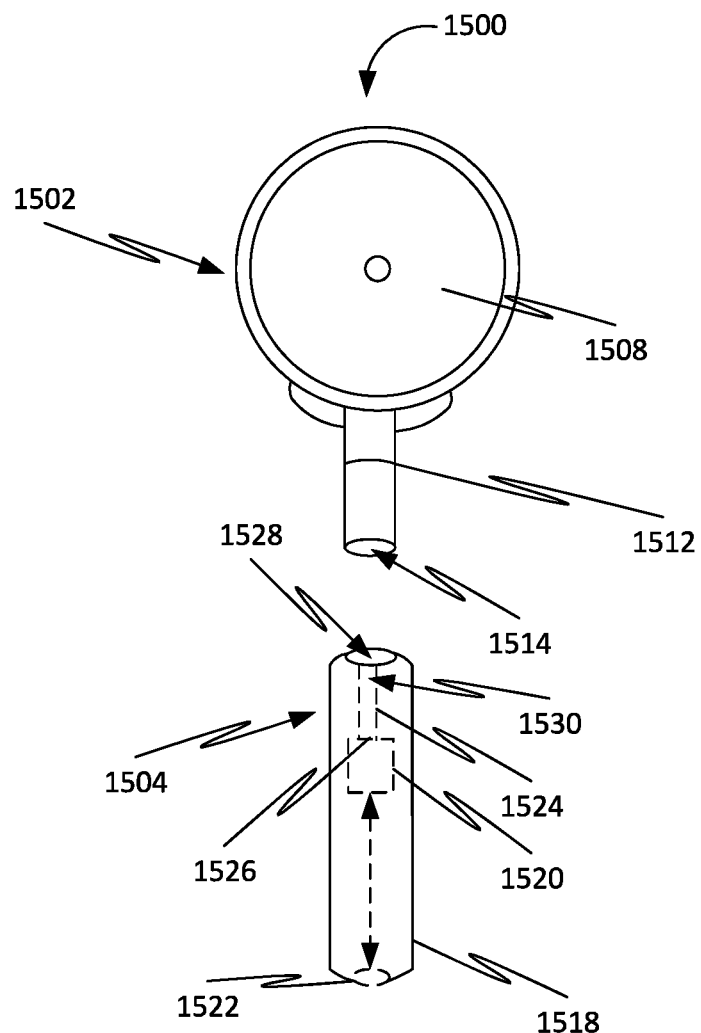
FIG. 15 is a top view of a stethoscope head assembly, in accordance with some embodiments.
Figure 15:
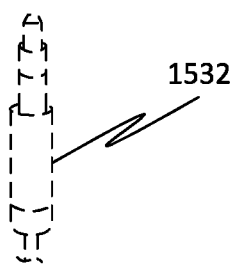
Figure 16:
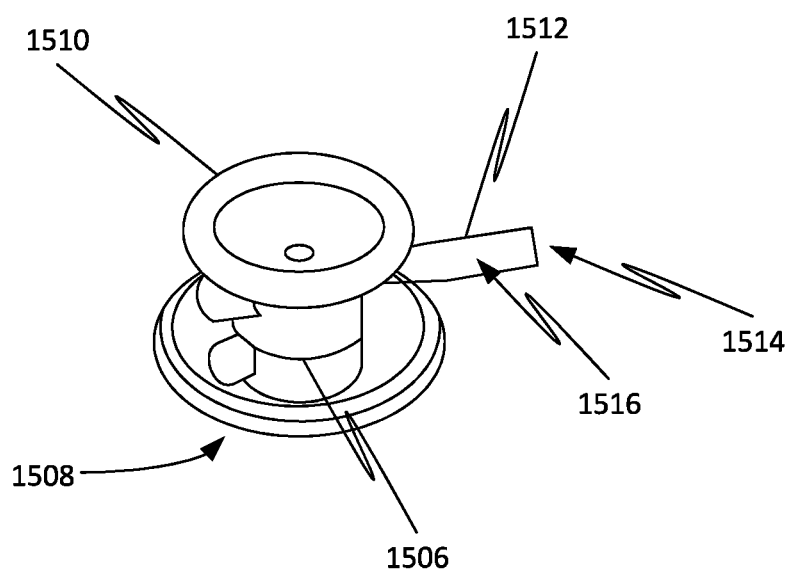
FIG. 16 is a rear perspective view of the chest piece of the stethoscope head assembly, in accordance with some embodiments.

FIG. 15 is a top view of a stethoscope head assembly 1500, in accordance with some embodiments. The stethoscope head assembly 1500 may include a chest piece 1502 and a body 1504. FIG. 16 is a rear perspective view of the chest piece 1502.

Further, the chest piece 1502 may include a cylindrical body 1506 (shown in FIG. 16) comprising an inner space.

Further, the chest piece 1502 may include a diaphragm 1508 disposed on a first side of the cylindrical body 1506. Further, the diaphragm 1508 may be configured to receive a first acoustic wave characterized by a first frequency.

Further, the chest piece 1502 may include a bell 1510 (shown in FIG. 16) disposed on a second side of the cylindrical body 1506. Further, the second side is opposing the first side. Further, the bell 1510 may be configured to receive a second acoustic wave characterized by a second frequency. Further, the second frequency may be lower than the first frequency.

Further, the chest piece 1502 may include a stem 1512 connected to the cylindrical body. Further, the stem 1512 may include a stem opening 1514 and a stem channel 1516 lucidly connecting the stem opening 1514 to the inner space.

Further, the body 1504 may include an exterior shell 1518 configured to form an interior space. Further, the body 1504 may include a microphone 1520 disposed in the interior space. Further, the microphone 1520 may be configured to convert an acoustic wave into an electrical sound signal.

Further, the body 1504 may include an electrical interconnect 1522 electrically coupled to the microphone 1520. Further, the electrical interconnect 1522 may be configured to be electrically coupled with an external electronic device (not shown) configured to process the electrical sound signal. Further, a part of the electrical interconnect 1522 may be disposed on the exterior shell 1518.

In an embodiment, the electrical interconnect 1522 may include a female port, wherein an audio jack 1532 attached to a cable (not shown)) may be inserted in the female port, wherein the cable may be connected to the external electronic device.

Figure 17:
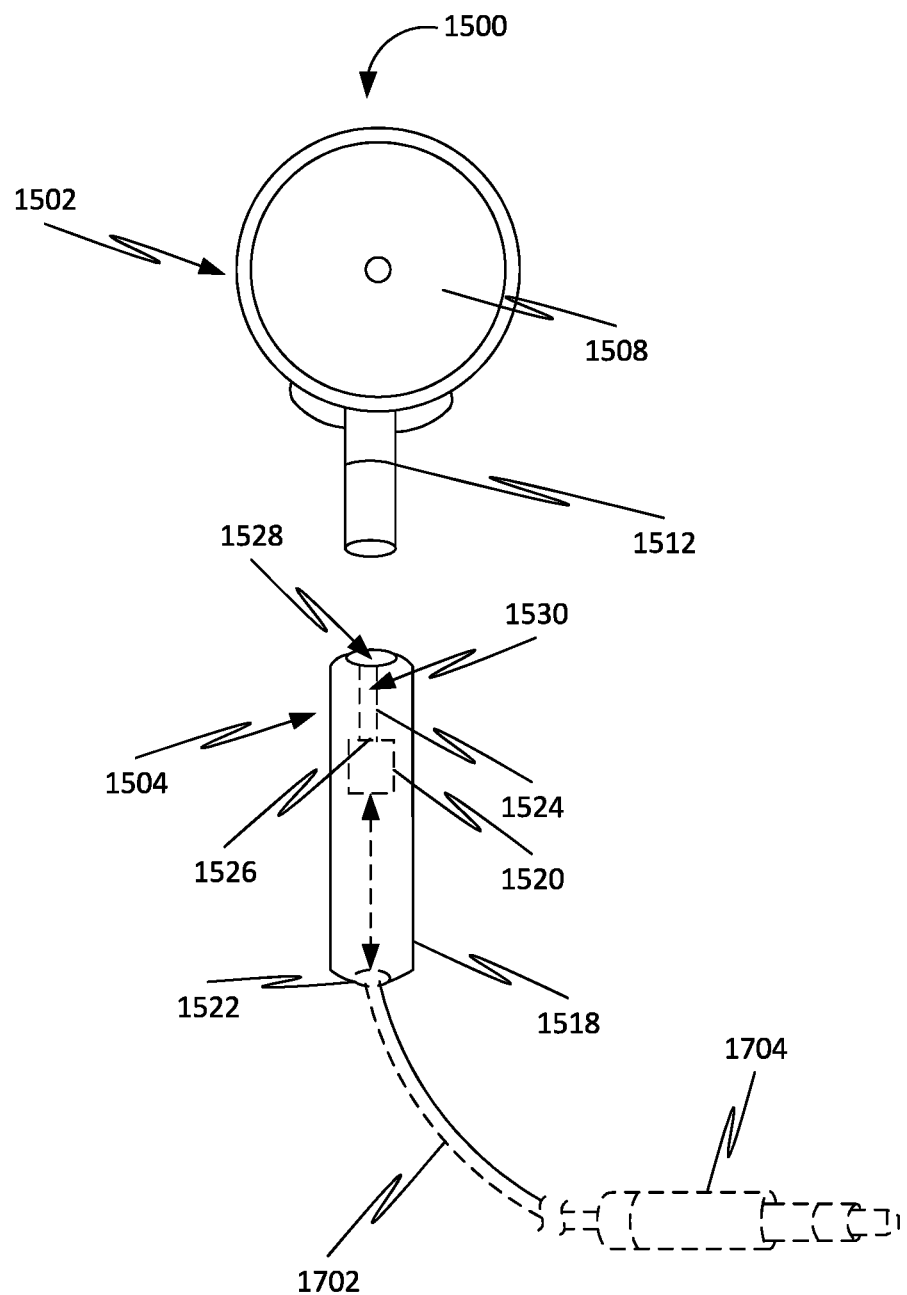
FIG. 17 is a top view of the stethoscope head assembly, in accordance with some embodiments.

In an embodiment, the electrical interconnect 1522 may include an electrical cable 1702 (shown in FIG. 17) and an audio jack 1704 electrically connected to a distal end of the electrical cable 1702. Further, the audio jack 1704 may be configured to removably interconnect with an audio port of the external electronic device.

Further, the body 1504 may include a conduit 1524 attached to the exterior shell 1518. Further, the conduit 1524 may include a first conduit opening 1526 and a second conduit opening 1528 and a conduit channel 1530 fluidly connecting the first conduit opening 1526 to the second conduit opening 1528. Further, the first conduit opening 1526 may be acoustically coupled to the microphone 1520. Further, the second conduit opening 1528 may be configured to be acoustically coupled to the stem opening 1514.

Figure 18:
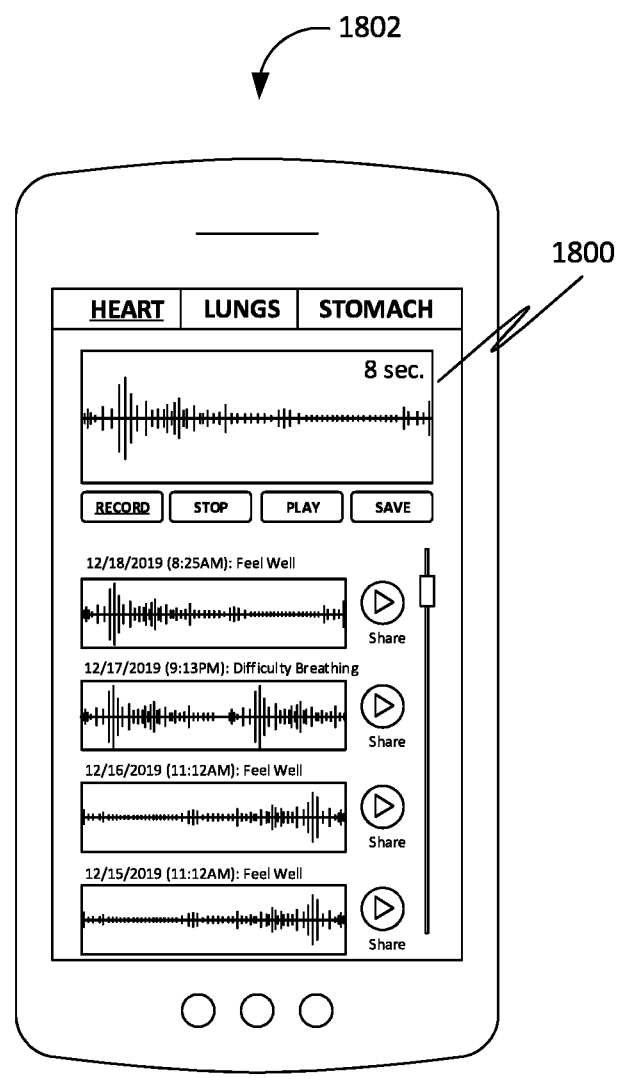
FIG. 18 is a schematic of a user interface of an application installed on an external electronic device receiving data from a stethoscope digital adapter, in accordance with some embodiments.

FIG. 18 is a schematic of a user interface 1800 of an application installed on an external electronic device 1802 receiving data from a stethoscope digital adapter, in accordance with some embodiments. The user interface 1800 may provide options to a user to perform one or more of recording, stopping and playing.

Figure 19:
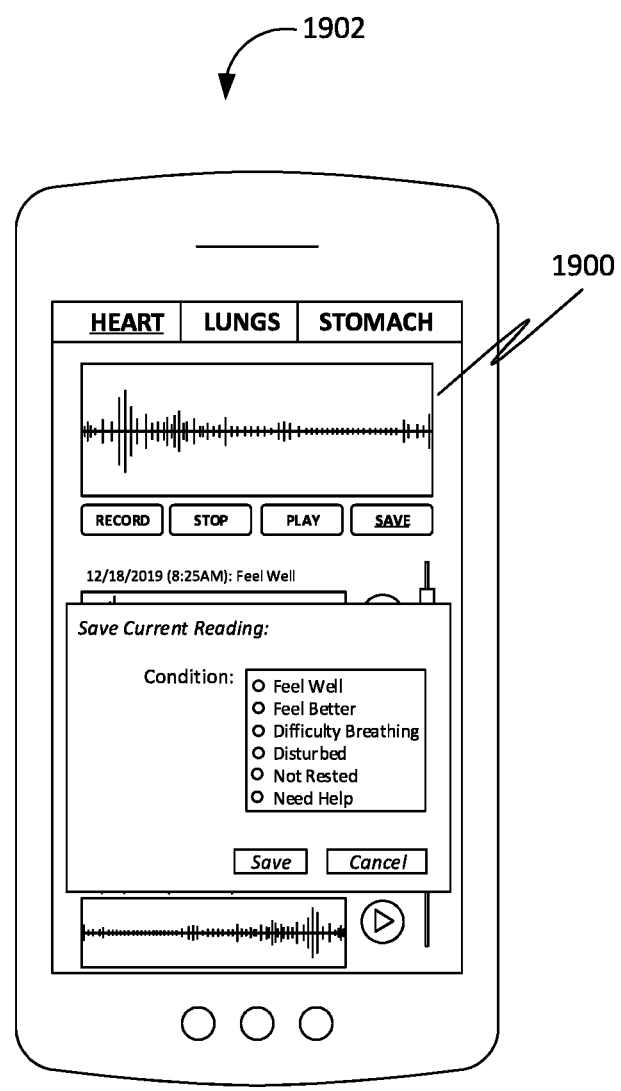
FIG. 19 is a schematic of a user interface of an application installed on an external electronic device receiving data from a stethoscope digital adapter, in accordance with some embodiments.

FIG. 19 is a schematic of a user interface 1900 of an application installed on an external electronic device 1902 receiving data from a stethoscope digital adapter, in accordance with some embodiments. The user interface 1900 may provide options to a user to perform saving operations.

Figure 20:
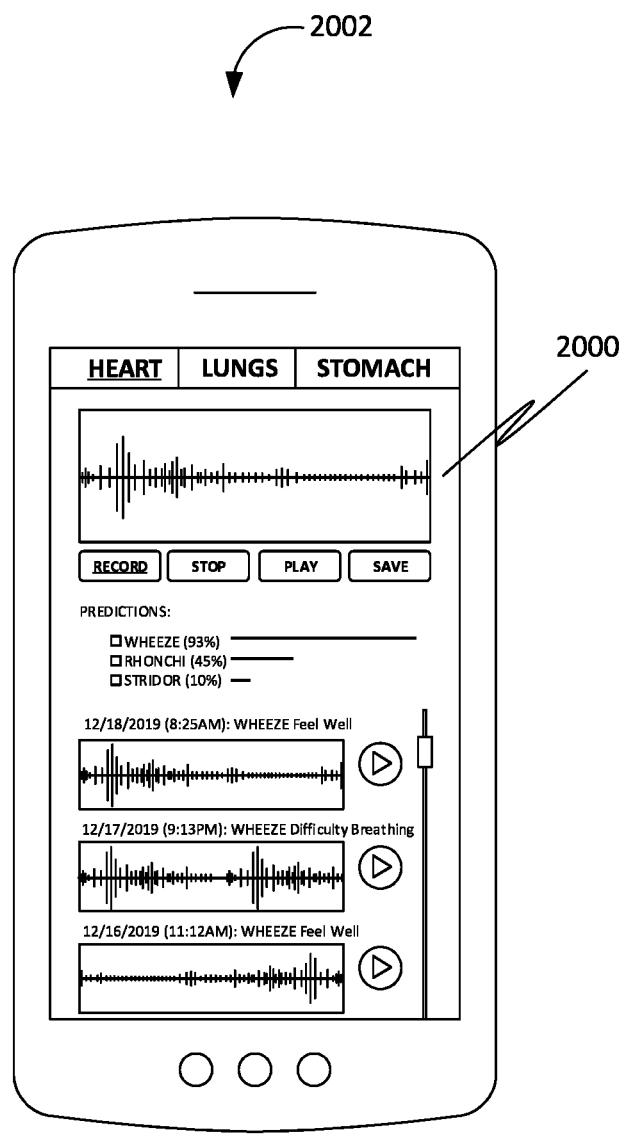
FIG. 20 is a schematic of a user interface of an application installed on an external electronic device receiving data from a stethoscope digital adapter, in accordance with some embodiments.

FIG. 20 is a schematic of a user interface 2000 of an application installed on an external electronic device 2002 receiving data from a stethoscope digital adapter, in accordance with some embodiments. The application may be configured to employ artificial intelligence and machine learning algorithms to perform predictions based on information received from the stethoscope digital adapter. The user interface 2000 may show predictions of possible health problem during recording.

Figure 21:
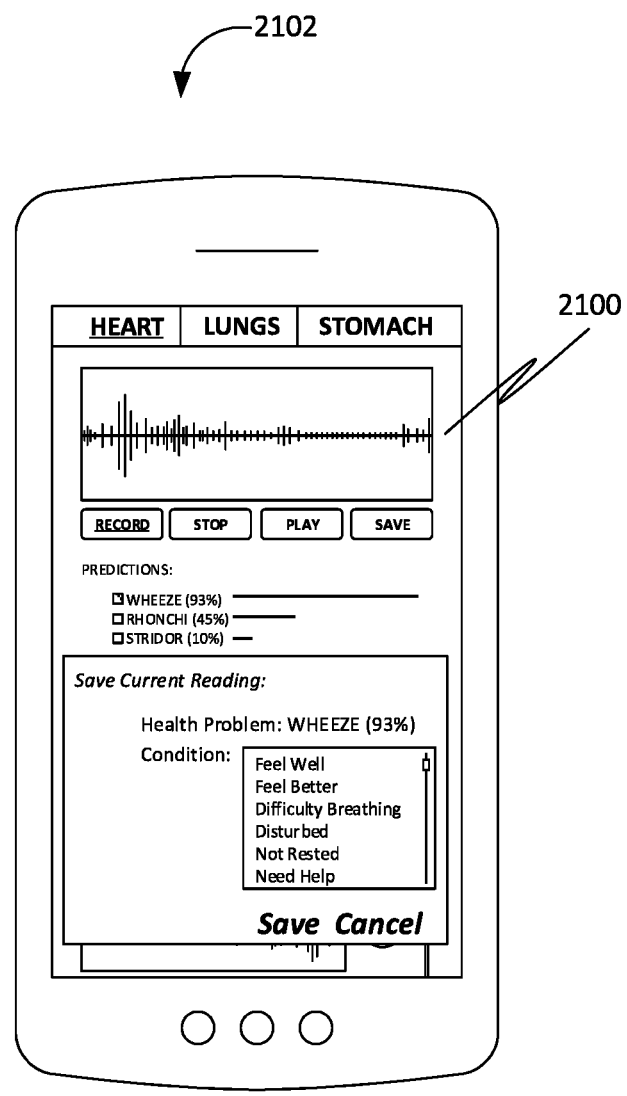
FIG. 21 is a schematic of a user interface of an application installed on an external electronic device receiving data from a stethoscope digital adapter, in accordance with some embodiments.

FIG. 21 is a schematic of a user interface 2100 of an application installed on an external electronic device 2102 receiving data from a stethoscope digital adapter, in accordance with some embodiments. The user interface 2100 may provide options to a user to perform saving operations for data including information about detected/predicted health problem (s).

Figure 22:
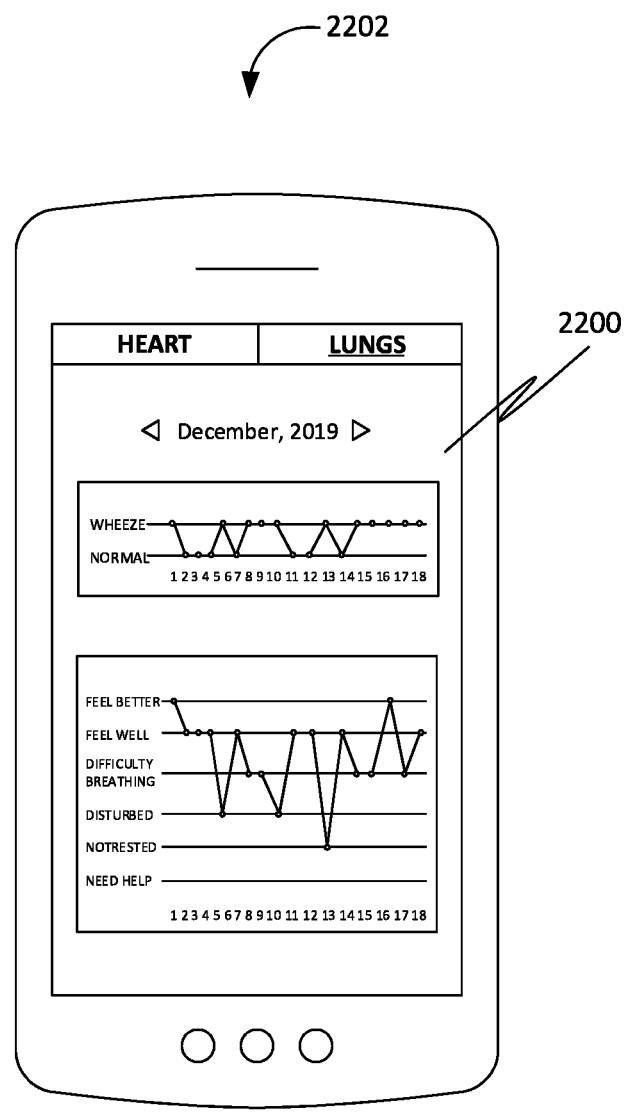
FIG. 22 is a schematic of a user interface of an application installed on an external electronic device receiving data from a stethoscope digital adapter, in accordance with some embodiments.

FIG. 22 is a schematic of a user interface 2200 of an application installed on an external electronic device 2202 receiving data from a stethoscope digital adapter, in accordance with some embodiments. The user interface 2200 may show historical data for a month.

Figure 23:
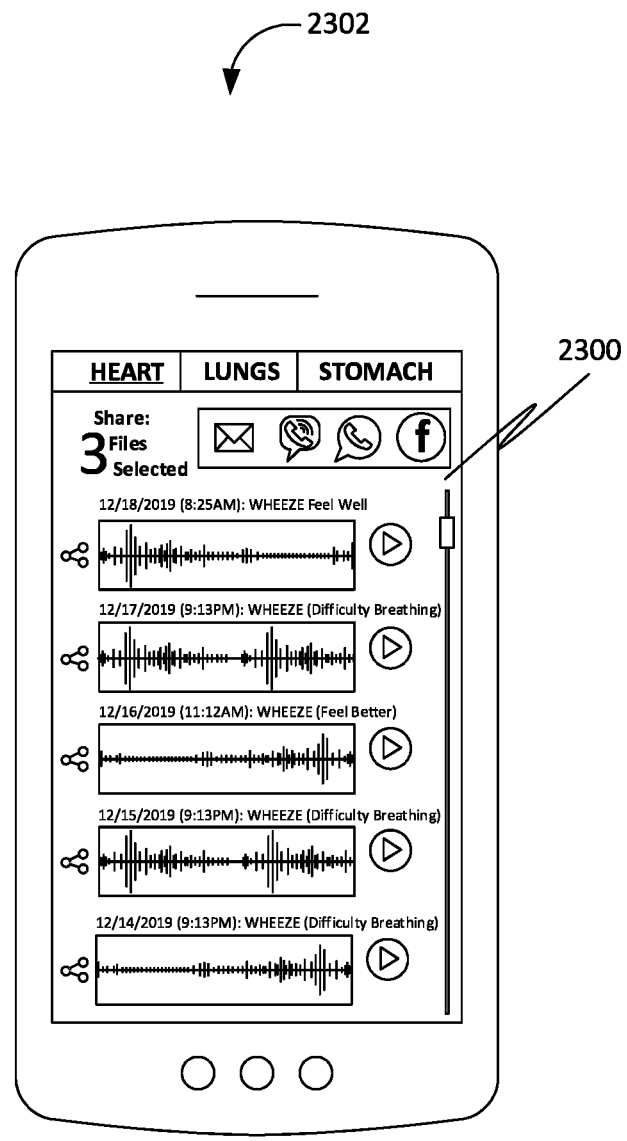
FIG. 23 is a schematic of a user interface of an application installed on an external electronic device receiving data from a stethoscope digital adapter, in accordance with some embodiments.

FIG. 23 is a schematic of a user interface 2300 of an application installed on an external electronic device 2302 receiving data from a stethoscope digital adapter, in accordance with some embodiments. The user interface 2300 may provide options to the user to share data.

Figure 24:
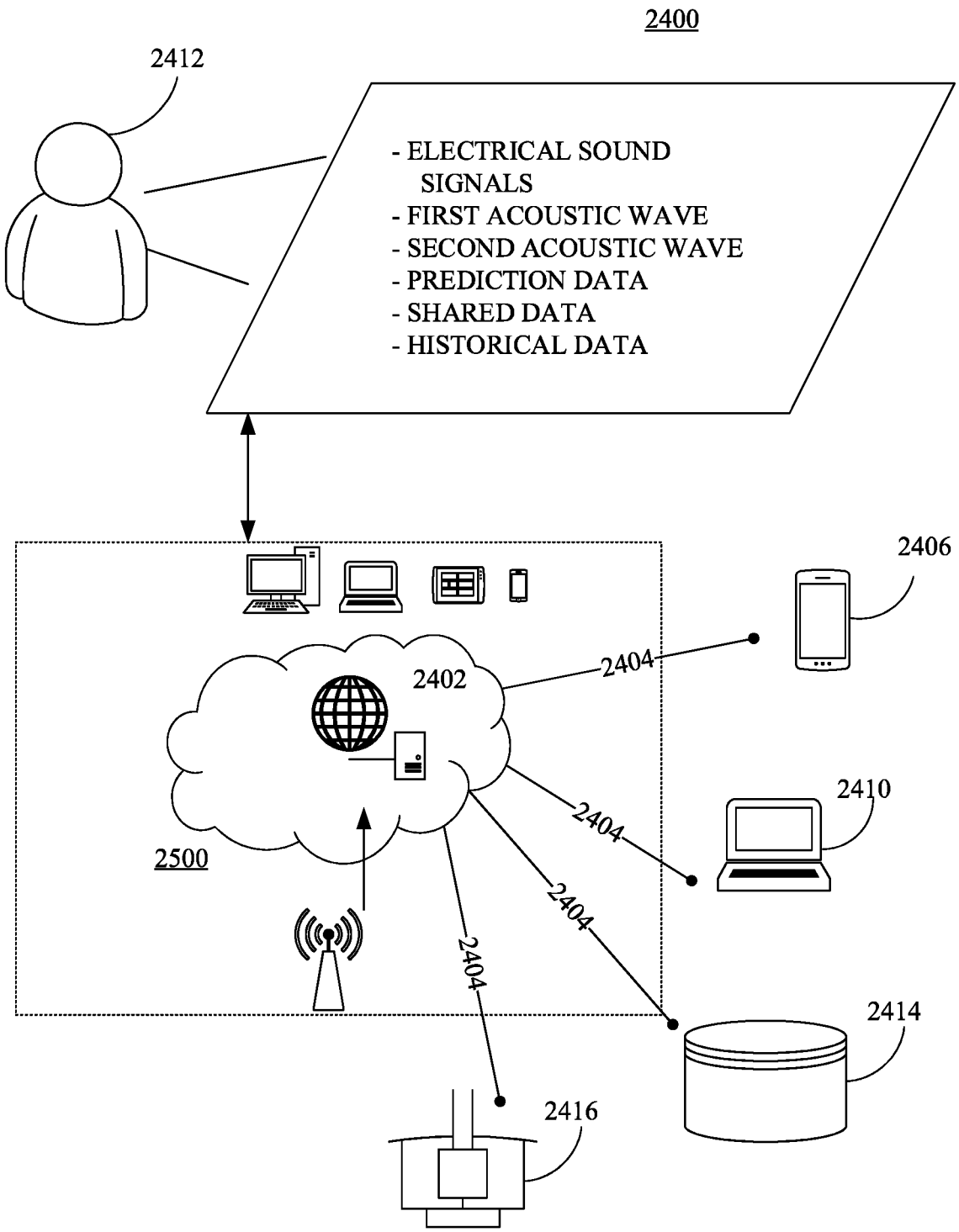
FIG. 24 is an illustration of an online platform consistent with various embodiments of the present disclosure.

FIG. 24 is an illustration of an online platform 2400 consistent with various embodiments of the present disclosure. By way of non-limiting example, the online platform 2400 to facilitate operation of a stethoscope digital adapter may be hosted on a centralized server 2402, such as, for example, a cloud computing service. The centralized server 2402 may communicate with other network entities, such as, for example, a mobile device 2406 (such as a smartphone, a laptop, a tablet computer, etc.), other electronic devices 2410 (such as desktop computers, server computers, etc.), databases 2414, stethoscope digital adapter 2416 over a communication network 2404, such as, but not limited to, the Internet. Further, users of the online platform 2400 may include relevant parties such as, but not limited to, end-users, individuals, care-givers, administrators, and so on. Accordingly, in some instances, electronic devices operated by the one or more relevant parties may be in communication with the platform.

A user 2412, such as the one or more relevant parties, may access online platform 100 through a web-based software application or browser. The web-based software application may be embodied as, for example, but not be limited to, a website, a web application, a desktop application, and a mobile application compatible with a computing device 2500.

Figure 25:
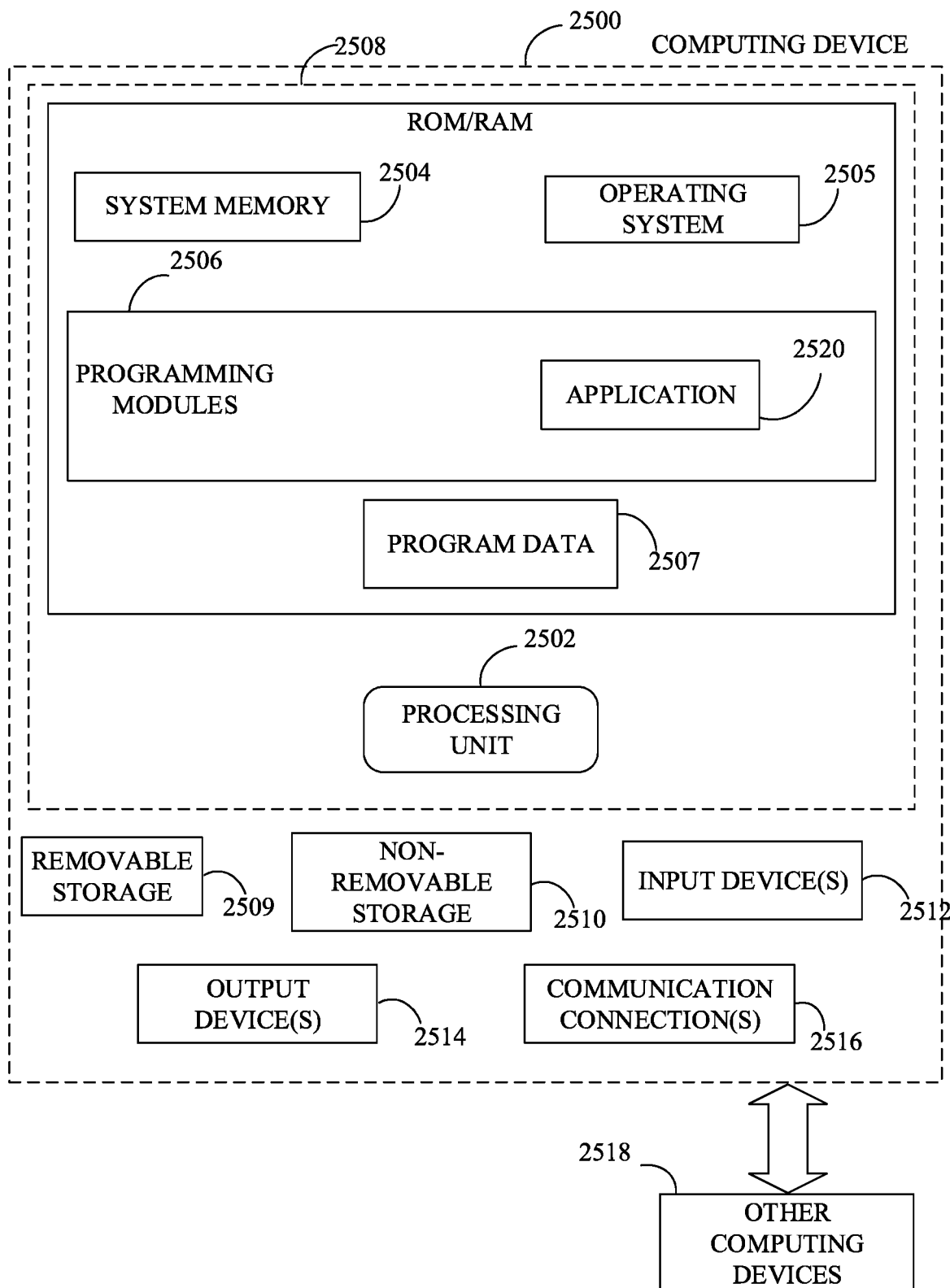
FIG. 25 is a block diagram of a computing device for implementing the methods disclosed herein, in accordance with some embodiments.

With reference to FIG. 25, a system consistent with an embodiment of the disclosure may include a computing device or cloud service, such as computing device 2500. In a basic configuration, computing device 2500 may include at least one processing unit 2502 and a system memory 2504. Depending on the configuration and type of computing device, system memory 2504 may comprise, but is not limited to, volatile (e.g. random-access memory (RAM)), non-volatile (e.g. read-only memory (ROM)), flash memory, or any combination. System memory 2504 may include operating system 2505, one or more programming modules 2506, and may include a program data 2507. Operating system 2505, for example, may be suitable for controlling computing device 2500's operation. In one embodiment, programming modules 2506 may include a data processing module, machine learning module, artificial intelligence module. Furthermore, embodiments of the disclosure may be practiced in conjunction with a graphics library, other operating systems, or any other application program and is not limited to any particular application or system. This basic configuration is illustrated in FIG. 25 by those components within a dashed line 2508.

Computing device 2500 may have additional features or functionality. For example, computing device 2500 may also include additional data storage devices (removable and/or non-removable) such as, for example, magnetic disks, optical disks, or tape. Such additional storage is illustrated in FIG. 25 by a removable storage 2509 and a non-removable storage 2510. Computer storage media may include volatile and non-volatile, removable and non-removable media implemented in any method or technology for storage of information, such as computer-readable instructions, data structures, program modules, or other data. System memory 2504, removable storage 2509, and non-removable storage 2510 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 2500. Any such computer storage media may be part of device 2500. Computing device 2500 may also have input device(s) 2512 such as a keyboard, a mouse, a pen, a sound input device, a touch input device, a location sensor, a camera, a biometric sensor, etc. Output device(s) 2514 such as a display, speakers, a printer, etc. may also be included. The aforementioned devices are examples and others may be used.

Computing device 2500 may also contain a communication connection 2516 that may allow device 2500 to communicate with other computing devices 2518, such as over a network in a distributed computing environment, for example, an intranet or the Internet. Communication connection 2516 is one example of communication media. Communication media may typically be embodied by computer-readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer-readable media as used herein may include both storage media and communication media.

As stated above, a number of program modules and data files may be stored in system memory 2504, including operating system 2505. While executing on processing unit 2502, programming modules 2506 (e.g., application 2520 such as a media player) may perform processes including, for example, one or more stages of methods, algorithms, systems, applications, servers, databases as described above. The aforementioned process is an example, and processing unit 2502 may perform other processes. Other programming modules that may be used in accordance with embodiments of the present disclosure may include machine learning applications.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general-purpose graphics processor-based systems, multiprocessor systems, microprocessor-based or programmable consumer electronics, application-specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer-readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid-state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

FIG. 23 is an illustration of a shelf system 2300 for facilitating advertising of a product, in accordance with some embodiments.

FIG. 24 is an illustration of a shelf system 2400 for facilitating advertising of a product, in accordance with some embodiments.

FIG. 25 is an illustration of a PCB (printed circuit board) 2500 of a shelf system for facilitating advertising of a product, in accordance with some embodiments. Further, the PCB 2500 may be embedded into shelves of the shelf system. Further, the PCB 2500 may accommodate 6 RFID, 6 Load cell, and a sonic sensor and touch sensor to provide different customer interactions and experiences. Further, the PCB 2500 may be configured to communicate to a server application hosted remotely and pull product information of the product to display to a customer using at least one display unit of the shelf system. Further, the PCB 2500 may include a Lithium Iron Phosphate battery that may charge and stay wireless of power supply to power electronics for over 10 hours.

Although the present disclosure has been explained in relation to its preferred embodiment, it is to be understood that many other possible modifications and variations can be made without departing from the spirit and scope of the disclosure.

The following is claimed:

1. A stethoscope digital adapter configured to enhance usability of an acoustic stethoscope, the stethoscope digital adapter comprising:
   a body comprising:
      an exterior shell configured to form an interior space;
      a microphone disposed in the interior space, wherein the microphone is configured to convert an acoustic wave into an electrical sound signal;
      an electrical interconnect electrically coupled to the microphone, wherein the electrical interconnect is configured to be electrically coupled with an external electronic device configured to process the electrical sound signal, wherein a part of the electrical interconnect is disposed on the exterior shell;
      a conduit attached to the exterior shell, wherein the conduit comprises a first conduit opening and a second conduit opening and a conduit channel fluidly connecting the first conduit opening to the second conduit opening, wherein the first conduit opening is acoustically coupled to the microphone, wherein the second conduit opening is configured to be acoustically coupled to a tube of the acoustic stethoscope; and
      a fastener attached to the body, wherein the fastener is configured to removably fasten the body to the tube of the acoustic stethoscope.

2. The stethoscope digital adapter of claim 1, wherein the conduit comprises a needle, wherein the second conduit opening is configured to pierce through the tube of acoustic stethoscope creating an opening in the tube.

3. The stethoscope digital adapter of claim 2 further comprising a sealing device removably fastened to the body, wherein the sealing device is configured to seal the opening created in the tube, wherein the sealing device is further configured to removably fasten to the tube of the acoustic stethoscope.

4. The stethoscope digital adapter of claim 2, wherein the opening is at most 1 millimeter (mm) in diameter.

5. The stethoscope digital adapter of claim 1, wherein the fastener comprises a pair of clamps, wherein a first clamp of the pair of clamps is disposed on a left side of the body, wherein a second clamp of the pair of clamps is disposed on a right side of the body, wherein each clamp of the pair of clamps is configured to receive and secure a corresponding portion of the tube.

6. The stethoscope digital adapter of claim 1, wherein the microphone comprises a MEMS microphone.

7. The stethoscope digital adapter of claim 1, wherein the microphone is characterized by a bandwidth ranging from 10 hertz (Hz) and 10 kilohertz (kHz).

8. The stethoscope digital adapter of claim 1, wherein the electrical interconnect is configured to receive electrical power from the external electronic device, wherein the microphone is configured to use the electrical power to convert the acoustic wave into the electrical sound signal.

9. The stethoscope digital adapter of claim 1, wherein the external electronic device comprises a mobile device.

10. The stethoscope digital adapter of claim 1, wherein the external electronic device comprises a patient monitoring device.

11. The stethoscope digital adapter of claim 1 further comprising the external electronic device, wherein the external electronic device comprises:
- an audio port configured to interconnect with the electrical interconnect, wherein the electrical interconnect comprises an electrical cable and an audio jack electrically connected to a distal end of the electrical cable, wherein the audio jack is configured to removably interconnect with the audio port;
- a processing device electrically coupled to the audio port, wherein the processing device is configured to:
  - generate digital sound data based on the electrical sound signal;
  - analyzing the digital sound data; and
  - identify at least one characteristic associated with the electrical sound signal based on the analyzing; and
- a display device communicatively coupled to the processing device, wherein the display device is configured to display the at least one characteristic.

12. The stethoscope digital adapter of claim 11, wherein the external electronic device further comprises a sound reproduction device communicatively coupled to the processing device, wherein the sound reproduction device is configured to generate amplified acoustic waves based on the digital sound data.

13. The stethoscope digital adapter of claim 12, wherein the processing device is further configured to shift at least one frequency of the digital sound data from an original value to a preferred value.

14. The stethoscope digital adapter of claim 13, wherein the at least one frequency comprises a band of frequencies from 10 Hz to 500 Hz, wherein the preferred value comprises 20 Hz to 600 Hz.

15. The stethoscope digital adapter of claim 12, wherein the at least one characteristic comprises an organ indicator associated with an organ originating the acoustic wave.

16. The stethoscope digital adapter of claim 15, wherein the processing device is configured for generating a file name associated with the data file based on each of the time-stamp, the organ indicator and a current condition tag, wherein the external electronic device further comprises an input device communicatively coupled to the processing device, wherein the input device is configured to receive the current condition tag, wherein the current condition tag is indicative of a medical condition of the user.

17. The stethoscope digital adapter of claim 16, wherein the processing device is further configured for generating the at least one characteristic based further on the current condition tag, wherein the at least one characteristic comprises one of a normal sound indication and an abnormal sound indication.

18. The stethoscope digital adapter of claim 17, wherein the predetermined quality threshold comprises a predetermined duration corresponding to the electrical sound signal.

19. The stethoscope digital adapter of claim 11, wherein the processing device is further configured to filter the digital sound data to cancel white noise present in the electrical sound signal.

20. The stethoscope digital adapter of claim 11 further comprising a storage device configured to save the digital sound data, the at least one characteristic and a time-stamp corresponding to the generation of the digital sound data in a data file, wherein the processing device is further configured to generate the time-stamp based on a real-time clock.

21. The stethoscope digital adapter of claim 11, wherein the processing device is further configured to:
- detect a quality of the electrical sound signal based on the analyzing; and
- generate a notification based on the quality being below a predetermined quality threshold, wherein the display device is configured for displaying the notification.

* * * * *